(12) United States Patent
Fairbanks et al.

(10) Patent No.: US 12,098,118 B2
(45) Date of Patent: Sep. 24, 2024

(54) ANALGESIC AND ANTI-ADDICTIVE COMPOSITIONS FOR TREATMENT OF CHRONIC PAIN AND OPIOID ADDICTION

(71) Applicant: Regents of the University of Minnesota, Minneapolis, MN (US)

(72) Inventors: Carolyn A. Fairbanks, Minneapolis, MN (US); Herbert T. Nagasawa, Minneapolis, MN (US); George L. Wilcox, Minneapolis, MN (US); Cristina D. Peterson, Minneapolis, MN (US); Kelley F. Kitto, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 711 days.

(21) Appl. No.: 17/291,345

(22) PCT Filed: Nov. 6, 2019

(86) PCT No.: PCT/US2019/060102
§ 371 (c)(1),
(2) Date: May 5, 2021

(87) PCT Pub. No.: WO2020/106454
PCT Pub. Date: May 28, 2020

(65) Prior Publication Data
US 2022/0002238 A1  Jan. 6, 2022

Related U.S. Application Data

(60) Provisional application No. 62/756,883, filed on Nov. 7, 2018.

(51) Int. Cl.
*C07C 279/24* (2006.01)
*C07C 279/14* (2006.01)

(52) U.S. Cl.
CPC .......... *C07C 279/24* (2013.01); *C07C 279/14* (2013.01)

(58) Field of Classification Search
None
See application file for complete search history.

(56) References Cited

U.S. PATENT DOCUMENTS

| 4,914,189 A | 4/1990 | Schally et al. |
| 6,150,419 A * | 11/2000 | Fairbanks ............... A61P 25/02 |
| | | 514/634 |

(Continued)

FOREIGN PATENT DOCUMENTS

| EP | 0135379 A2 | 3/1985 |
| WO | 1994029269 A1 | 12/1994 |

(Continued)

OTHER PUBLICATIONS

Dempsey et al., Sci Rep. Oct. 18, 2017;7(1):13432 (Year: 2017).*

(Continued)

*Primary Examiner* — Jeffrey S Lundgren
*Assistant Examiner* — Anthony Joseph Seitz
(74) *Attorney, Agent, or Firm* — Viksnins Harris Padys Malen LLP

(57) ABSTRACT

The invention provides a compound of formula I and stereoisomers, tautomers, or pharmaceutically acceptable salts thereof, and with the substituents and structural features described herein. Also described are pharmaceutical compositions and medicaments that include the formula I compounds, as well as methods of using such as therapeutic agents for the treatment of pain-related disorders and diseases and in combination with other therapeutic agents.

(Continued)

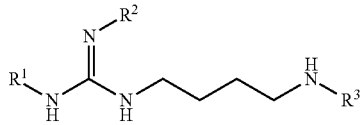

5 Claims, 15 Drawing Sheets

(56) References Cited

U.S. PATENT DOCUMENTS

| | | |
|---|---|---|
| 2005/0159362 A1 | 7/2005 | Sircar et al. |
| 2015/0182479 A1 | 7/2015 | Glynn et al. |

FOREIGN PATENT DOCUMENTS

| | | | | |
|---|---|---|---|---|
| WO | WO-2010000073 A1 * | 1/2010 | ........... | A61K 31/538 |
| WO | 2011033296 A1 | 3/2011 | | |
| WO | 2018226732 A1 | 12/2018 | | |

OTHER PUBLICATIONS

Wiley et al., Bioorganic & Medicinal Chemistry Letters, vol. 5, Issue 23, 1995, pp. 2835-2840 (Year: 1995).*
Yokoi et al., Neurochem Res 21, 1187-1192 (1996) (Year: 1996).*
He, H., et al., "Synthesis and Analgesic Activity Evaluation of Some Agmatine Derivatives", Molecules 11, 393-402 (2006).
Tricot, C., et al., "Comparative Studies on the Degradation of Guanidino and Ureido Compounds By Pseudomonas", Journal of General Microbiology 136, 2307-2317 (1990).
Wakimoto, T., et al., "Structure-activity relationship study on α1 adrenergic receptor antagonists from beer", Bioorg. Med. Chem. Lett. 19, 5905-5908 (2009).
Dijols, S., et al., "First Non-alpha-Amino Acid Guanidines Acting as Efficient NO Precursors upon Oxidation by NO Synthase II or Activated Mouse Macrophages", Biochemistry 41, 9286-9292 (2002).
Fairbanks, C., et al., "Agmatine reverses pain induced by inflammation, neuropathy, and spinal cord injury", PNAS 97 (19), 10584-10589 (2000).
Kitto, K., et al., "Supraspinally administered agmatine prevents the development of supraspinal morphine analgesic tolerance", European Journal of Pharmacology 536 (1-2), 133-137 (2006).
Morgan, A., et al., "Effects of agmatine on the escalation of intravenous cocaine and fentanyl self-administration in rats", Pharmacology Biochemistry and Behavior 72, 873-880 (2002).
Patent Cooperation Treaty, International Searching Authority, Search Report and Written Opinion for PCT/US2019/060102, 11 pages, dated Jun. 19, 2020.
Piletz, J., et al., "Agmatine: clinical applications after 100 years in translation", Drug Discov Today 18 (17-18), 880-893 (2013).
PUBCHEM, "Agmatine", CID-199, 38 pages, Sep. 16, 2004.
Su, R, et al., "A biphasic opioid function modulator: agmatine", Acta Pharmacol Sin 24 (7), 631-636 (2003).
Waataja, J., et al., "Agmatine preferentially antagonizes GluN2B-containing N-methyl-d-aspartate receptors in spinal cord", J Neurophysiol 121, 662-671 (2019).
Wade, C., et al., "Immunoneutralization of Agmatine Sensitizes Mice to μ-Opioid Receptor Tolerance", Journal of Pharmacology and Experimental Therapeutics 331 (2), 539-546 (2009).
Wade, C., et al., "Supraspinally-administered agmatine attenuates the development of oral fentanyl self-administration", European Journal of Pharmacology 587, 135-140 (2008).
Yezierski, R., et al., "Neuroprotective effects of agmatine following spinal cord injury", Society for Neuroscience Abstracts 24 (1), 1998.
Yu, C., et al., "Agmatine improves locomotor function and reduces tissue damage following spinal cord injury", Neuroreport 11 (14), 3203-3207 (2000).
Yu, C, et al., "Effects of Agmatine, Interleukin-10, and Cyclosporin on Spontaneous Pain Behavior After Excitotoxic Spinal Cord Injury in Rats", Journal of Pain 4 (3), 129-140 (2003).

* cited by examiner

ANALGESIC AND ANTI-ADDICTIVE COMPOSITIONS FOR TREATMENT OF CHRONIC PAIN AND OPIOID ADDICTION

CROSS REFERENCE TO RELATED APPLICATION

This application claims priority to U.S. Provisional Application No. 62/756,883 filed on 7 Nov. 2018, which is incorporated by reference herein.

GOVERNMENT FUNDING

This invention was made with government support under W81XWH-15-1-0494 awarded by the Department of the Army. The government has certain rights in the invention.

FIELD OF THE INVENTION

Described herein are compounds, including pharmaceutically acceptable salts, metabolites, pharmaceutical compositions comprising such compounds, and methods of using such compounds to treat chronic pain and opioid addiction, or in combination with other therapeutic agents.

BACKGROUND OF THE INVENTION

Despite decades of sophisticated targeting of molecular systems identified as important for chronic pain, management of chronic pain remains an area in acute need of new approaches. Practitioner and patient enthusiasm for chronic pharmacological treatment with opioid receptor agonists (the most effective analgesics) and NSAIDS (the most widely used analgesics) is diminishing rapidly due to serious concerns regarding respiratory depression, diversion and addiction, and toxicity (NSAIDS). Options for patients in need of chronic treatment for pain control are, consequently, increasingly limited.

The Institute of Medicine has estimated that chronic pain costs the US economy $600 billion annually in health care and lost productivity costs. It is estimated that 25 million inpatient surgeries and 35 million ambulatory care surgeries are performed every year in the United States. It is estimated that about 60% of these patients will experience moderate, severe or extreme pain. Although prescription opioid analgesics, such as morphine, fentanyl, hydrocodone and oxycodone, are the gold standard for management of chronic, post-surgical and post-traumatic pain, distribution of these drugs to unintended recipients (diversion), addiction and respiratory depression (culminating in tens of thousands of overdose-induced deaths annually) constitute a huge, current societal problem. Additionally, it is estimated that less than half of those postoperative patients receive sufficient pain relief, a situation that can give rise to longer-lasting persistent pain.

In response to this declared epidemic of opioid abuse, diversion and lethality, the Centers for Disease Control (CDC) issued a 12-point Opioid-Prescribing Guideline in March of 2016. Based on the dangers of long-term opioid therapy, the guideline recommends consideration of alternatives to opioids and limitations to dosage for chronic pain, limitations to the duration of treatment for acute pain, and careful attention to risk factors accompanying opioid use. Because opioid addiction potential derives from actions in reward centers of the brain and respiratory depression from actions in the brainstem, targeting non-opioid analgesic or anti-hyperalgesic targets represents an effective method to avoid these liabilities.

Non-opioid analgesic substances and opioid adjuvants may serve the goal of limiting opioid analgesic tolerance (and dose requirements), dependence, and addiction when opioid analgesic therapy remains necessary. Because opioid addiction potential derives from actions in the mesolimbic dopaminergic system and respiratory depression from actions in the brainstem, alternative non-opioid analgesics are greatly needed.

Nearly twenty years of pharmacological studies have consistently shown that antagonism of the NMDA (N-methyl D-aspartate) receptor or inhibition of the nitric oxide synthase (NOS) enzyme reduces signs of chronic pain in pre-clinical models. Some limited clinical translation has occurred through evaluation of the efficacy of the use of ketamine and dextromethorphan in various pain conditions, but the outcomes have been conflicting. Similarly, the use of clinically available NMDA receptor antagonists has not led to effective treatments due to a range of adverse effects (cognition, sedation, motor function) or undesirable inhibition of physiological neuroplasticity, manifest in learning and memory. It has been proposed that these side effects are associated with nonsubtype-selective or high affinity NMDA receptor antagonists. Other low affinity (memantine, amantadine) or NMDA receptor subunit 2B- (NR2B) selective antagonists like ifenprodil are proposed as more effective with a higher therapeutic index. Such compounds may prove to be effective and important alternatives to opioids for pain management.

The decarboxylated form of L-arginine, known as agmatine (1-(4-aminobutyl)guanidine, CAS Registry Number: 306-60-5), also antagonizes the NMDA receptor in a manner that is NR2B subunit-selective (Waataja, J J et al., *J. Neurophysiol.* (2019) 121(2): 662-671). Agmatine inhibits NMDA-evoked current and behavior as well as nitric oxide production. Agmatine also inhibits the development of chronic pain, but without the associated motor toxicity commonly observed with NMDA receptor antagonists (Fairbanks, C A et al., *Proc. Natl. Acad Sci. USA* (2000) 97(19): 10584-10489). Agmatine reduces manifestations of chronic pain in mice. Therefore, development of agmatine or strategically-substituted agmatine derivatives could provide an effective therapy for pain with potentially limited side effects. Agmatine reduces or prevents opioid-induced tolerance and dependence when given either systemically or centrally (Piletz, J E et al (2013) *Drug Disc. Today* 18(17-18):880-893; Fairbanks, C A and Wilcox, G L, *J. Pharmacol. Exp. Ther.* (1997) 282(3): 1406-1417; Wade, C L et al., *J. Pharmacol. Exp. Ther.* (2009) 331(2): 539-546). Agmatine also reduces fentanyl self-administration when administered systemically (Morgan, A D et al (2002) *Pharmacol. Biochem. and Behav.* 72:873-880) or intracerebroventricularly (Wade, C L et al (2008) *Eur. J. Pharmacol.* 587:135-140). Development of agmatine as a pharmacotherapeutic has been limited to consideration as a nutritional supplement based on the fact that it is an endogenous molecule.

Agmatine and its analogs may produce anti-hyperalgesic effects through the NR2B receptor subunit of the NMDA receptor as one possible mechanism of action. This subunit has been demonstrated to have lower incidence of motor side effects, a side effect that has limited the development of other NMDA receptor antagonists that are clinically available. N-(4-guanidinobutyl)acetamide has been reported (*Chem. Abs* 63, 9737 (1965): Nippon Nogai Kagaklu Kaishi 33:679 (1959)

Systemic delivery of new chemical agmatine entities may cross the blood brain barrier more readily and achieve an analgesic outcome with greater potency. Such compositions may be useful as pharmacological agents for chronic pain management.

Currently there is a need for non-addictive and effective therapeutic agents useful for relief of neuropathic or inflammatory pain.

SUMMARY OF THE INVENTION

In one aspect the present invention provides acylated 1-(4-aminobutyl)guanidine compounds having analgesic activity and are useful for treatment related to pain management and addiction.

Accordingly, the invention provides acylated 1-(4-aminobutyl)guanidine compounds of formula I:

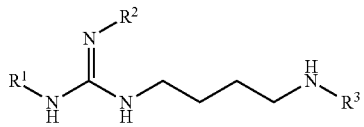

wherein:
$R^1$ and $R^2$ are independently selected from a group consisting of H, C(=O)OR$^a$, and C(=O)R$^a$;
$R^3$ is selected from a group consisting of H, C(=O)OR$^a$, and C(=O)R$^b$;
where at least one of $R^1$, $R^2$ and $R^3$ is not H;
$R^a$ is ($C_1$-$C_{12}$) alkyl;
$R^b$ is selected from a group consisting of ($C_1$-$C_{12}$) alkyldiyl-CO$_2$H, ($C_1$-$C_{12}$) alkyldiyl-CH(CO$_2$H)NH$_2$; ($C_1$-$C_{12}$) alkyldiyl-CH(CO$_2$H)NHC(=O)($C_1$-$C_{12}$) alkyldiyl-CH(CO$_2$H)NH$_2$; and SR$^c$;
$R^c$ is ($C_1$-$C_{12}$) alkyldiyl-CH(C(=O)R$^d$)NHC(=O)($C_1$-$C_{12}$) alkyldiyl-CH(CO$_2$H)NH$_2$; and
$R^d$ is C(=O)NH($C_1$-$C_{12}$) alkyldiyl-CO$_2$H;
where alkyl and alkyldiyl are independently and optionally substituted with one or more groups selected from F, Cl, Br, I, —CN, —CO$_2$H, NH$_2$, —NHCH$_3$, —N(CH$_3$)$_2$, —NHCOCH$_3$, —OH, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, and —S(O)$_3$H,
or a pharmaceutically acceptable salt thereof;

The invention also provides a pharmaceutical composition comprising a compound of formula I or a pharmaceutically acceptable salt thereof, and a pharmaceutically acceptable carrier, glidant, diluent, or excipient.

The invention also provides a method for treating or preventing opioid analgesic tolerance, neuropathic pain, and opioid analgesic addiction in an animal (e.g., a mammal such as a human) comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of opioid analgesic tolerance, neuropathic pain, and opioid analgesic addiction.

The invention also provides the use of a compound of formula I or a pharmaceutically acceptable salt thereof to prepare a medicament for treating opioid analgesic tolerance, neuropathic pain, and opioid analgesic addiction in an animal (e.g. a mammal such as a human).

The invention also provides processes and intermediates disclosed herein that are useful for preparing a compound of formula I or a salt thereof.

BRIEF DESCRIPTION OF THE DRAWINGS

FIG. 6A shows control mice injected IV with saline. FIG. 6B shows mice injected IP with compound J-4 from Table 2. Open symbols represent the lever pressing of mice on the "control" lever that result in no reward. Solid symbols represent the lever pressing of mice on the "active lever" which results in delivery of a 70 µL volume of oxycodone into a receptacle. The mice lick or drink the opioid from the receptacle. Mice pre-treated prior to session with control vehicle (saline), demonstrate greater lever pressing on the "active lever" or that which delivers oxycodone. In contrast, those subjects that receive an intraperitoneal injection of J-4 prior to the session demonstrate substantially reduced preference for the active lever versus the control lever. These experimental groups were run concurrently under identical conditions and suggest that the formula I compound J-4 reduced the development of opioid addiction.

DETAILED DESCRIPTION OF EXEMPLARY EMBODIMENTS

Figure 1A:
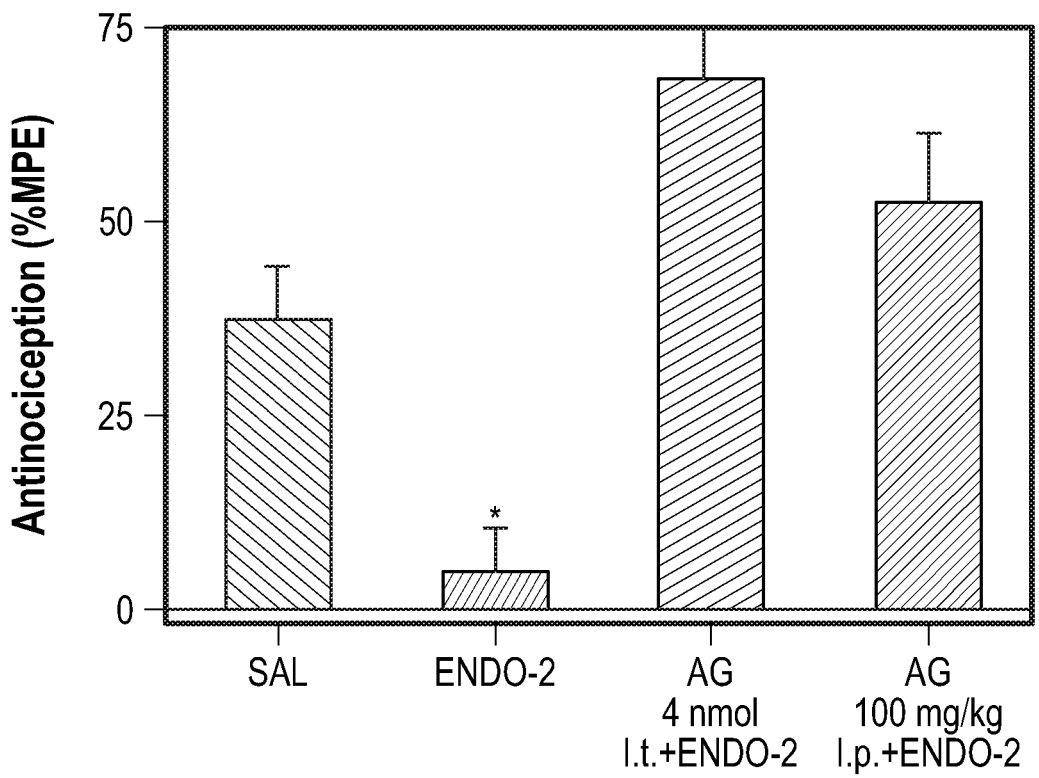
FIG. 1A shows a dose of endomorphin-2 (ENDO-2) was given that results in an analgesic effect, SAL (first bar from left). This group of mice had previously received an intrathecal injection of saline as a control to the subjects represented by ENDO-2 (second bar from left) which had an intrathecal pre-treatment of ENDO-2. When that second group received a second injection of ENDO-2 (same dose as in the SAL group), the analgesic effect was not observed. Analgesic tolerance to ENDO-2 was, therefore, induced. However, when intrathecal agmatine is co-administered with that same tolerance-inducing pre-treatment intrathecal dose of ENDO-2, the second dose of ENDO-2 demonstrates robust analgesia. AG 4 nmol (third bar from left). The inclusion of agmatine, therefore, protected against the induction of opioid tolerance. This relationship was also true when 100 mg/kg agmatine was delivered systemically (i.p., intraperitoneal) at the same time as the initial dose of intrathecal ENDO-2 (fourth bar from left).

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

Definitions

The term "halo" or "halogen" is fluoro, chloro, bromo, or iodo.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_{12})$alkyl. $(C_1-C_8)$alkyl, $(C_2-C_8)$alkyl, $(C_1-C_6)$alkyl. $(C_2-C_6)$alkyl, $(C_3-C_6)$alkyl, and the like. Examples of alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C$ ($CH_3$)$_2$CH($CH_3$)$_2$), 3,3-dimethyl-2-butyl (—CH($CH_3$)C($CH_3$)$_3$), 1-heptyl, 1-octyl, and higher homologs and isomers.

The term "alkyldiyl" as used herein refers to a saturated linear or branched-chain divalent hydrocarbon radical of about one to twelve carbon atoms ($C_1$-$C_{12}$), wherein the alkyldiyl radical may be optionally substituted independently with one or more substituents described below. In another embodiment, an alkyldiyl radical is one to eight carbon atoms ($C_1$-$C_8$), or one to six carbon atoms ($C_1$-$C_6$). Examples of alkyldiyl groups include, but are not limited to, methylene (—$CH_2$—), ethylene (—$CH_2CH_2$—), propylene (—$CH_2CH_2CH_2$—), and the like. An alkyldiyl group may also be referred to as an "alkylene" group.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkoxy" refers to an alkyl group attached to the remainder of the molecule via an oxygen atom ("oxy").

The term "alkylthio" refers to an alkyl groups attached to the remainder of the molecule via a thio group.

The term "cycloalkyl" refers to a saturated or partially unsaturated (non-aromatic) all carbon ring having 3 to 8 carbon atoms (i.e., ($C_3$-$C_8$)carbocycle). The term also includes multiple condensed, saturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g. tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g., spiropentane, spiro[4,5]decane, and others), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc.). Non-limiting examples of cycloalkyls include cyclopropyl, cyclobutyl, cyclopentyl, cyclohexyl, bicyclo[2.2.1]heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein, the term "heteroatom" is meant to include oxygen (O), nitrogen (N), sulfur (S) and silicon (Si).

As used herein a wavy line "∼" that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. The terms "treat", "treatment", or "treating" can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention.

"Intrathecal" administration is a route of administration for compounds of the invention via an injection into the spinal canal, or into the subarachnoid space so that it reaches the cerebrospinal fluid (CSF) and is useful in pain management applications. The drug needs to be given this way to avoid being stopped by the blood brain barrier. The same drug given orally must enter the blood stream and may not be able to pass out and into the brain. Drugs given by the intrathecal route often have to be made up specially by a pharmacist or technician because they cannot contain any preservative or other potentially harmful inactive ingredients that are sometimes found in standard injectable drug preparations. Thus formulations for intrathecal administration are likely to be substantially different than formulations for systemic administration. Delivery systems for opioid analgesics have been reviewed in Leppert, W. et al (2013) *Current Pharmaceutical Design,* 19(41):7271-7293; Reig, E. et al (2009) *Neuromodulation,* 1:467-481, Eds. Krames, E. et al, Elsevier, London, UK; Nguyen, H. et al (2003) *Anesthesiology Clinics of North America.* 21(4):805-816, which are incorporated by reference for their specific teaching.

The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen. S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties. e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons. The compounds disclosed herein can also exist as tautomeric isomers in certain cases. Although only one delocalized resonance structure may be depicted, all such forms are contemplated within the scope of the invention.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)NH$_2$) or acetyl group). The open valence can also be created by the chemical conversion of a first function group of the compound to a second functional group of the compound (e.g., reduction of a carbonyl group, replacement of a carbonyl group with an amine) followed by the removal of 1 or more atoms from the second functional group to create the open valence.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Acylated 1-(4-Aminobutyl)Guanidine Compounds

The present invention provides acylated 1-(4-aminobutyl) guanidine compounds of formula I, and pharmaceutical formulations thereof, which are potentially useful in the treatment of pain, having the structure:

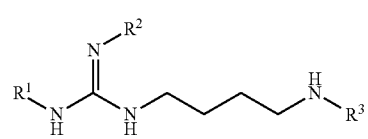

I wherein:
R$^1$ and R$^2$ are independently selected from a group consisting of H, C(=O)OR$^a$, and C(=O)R$^a$;
R$^3$ is selected from a group consisting of H, C(=O)OR$^a$, and C(=O)R$^b$;
where at least one of R$^1$, R$^2$ and R$^3$ is not H;
R$^a$ is (C$_1$-C$_{12}$) alkyl;
R$^b$ is selected from a group consisting of (C$_1$-C$_{12}$) alkyldiyl-CO$_2$H, (C$_1$-C$_{12}$) alkyldiyl-CH(CO$_2$H)NH$_2$; (C$_1$-C$_{12}$) alkyldiyl-CH(CO$_2$H)NHC(=O)(C$_1$-C$_2$) alkyldiyl-CH(CO$_2$H)NH$_2$; and SR$^c$;
R$^c$ is (C$_1$-C$_{12}$) alkyldiyl-CH(C(=O)R$^d$)NHC(=O)(C$_1$-C$_{12}$) alkyldiyl-CH(CO$_2$H)NH$_2$; and
R$^d$ is C(=O)NH(C$_1$-C$_{12}$) alkyldiyl-CO$_2$H;
where alkyl and alkyldiyl are independently and optionally substituted with one or more groups selected from F, Cl, Br, I, —CN, —CO$_2$H, NH$_2$. —NHCH$_3$, —N(CH$_3$)$_2$, —NHCOCH$_3$, —OH, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O) (OH)$_2$, —S(O)$_2$N(CH$_3$)$_2$, —SCH$_3$, —S(O)$_2$CH$_3$, and —S(O)$_3$H,
or a pharmaceutically acceptable salt thereof:

Exemplary embodiments of formula I compounds include wherein R$^1$ is selected from C(=O)OCH$_2$CH$_3$ and C(=O)OC(CH$_3$)$_3$.

Exemplary embodiments of formula I compounds include wherein R$^2$ is selected from C(=O)OCH$_2$CH$_3$.

Exemplary embodiments of formula I compounds include wherein R$^3$ is selected from C(=O)OCH$_2$CH$_3$. C(=O)CH$_3$, and C(=O)(CH$_2$)$_{10}$—CO$_2$H.

Embodiments of the invention include the formula I compounds of Table 2.

TABLE 2

Exemplary formula I compounds

| No. | Structure | IUPAC Name | Mass spec M + H |
|---|---|---|---|
| J-1 | 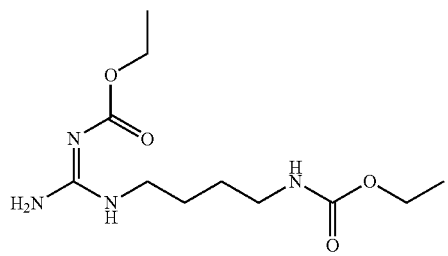 [SMILES: CCOC(=O)/N=C(/N)NCCCCNC(=O)OCC] | ethyl (amino((4-((ethoxycarbonyl)amino)butyl)amino)methylene)carbamate | 275.2 |
| J-2 | 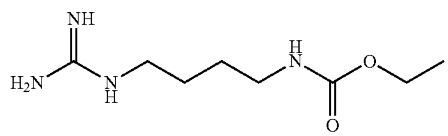 | ethyl (4-guanidinobutyl)carbamate | 203.1 |
| J-3 | 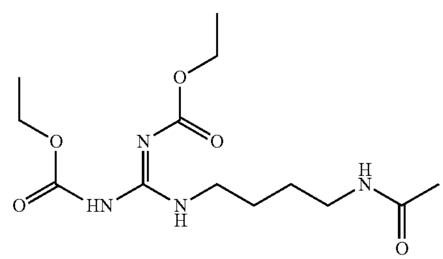 [SMILES: CCOC(=O)/N=C(\NCCCCNC(C)=O)NC(=O)OCC] | 4-(2,3-bis(ethoxycarbonyl)guanidino)butylacetamide | 317.2 |
| J-4 | 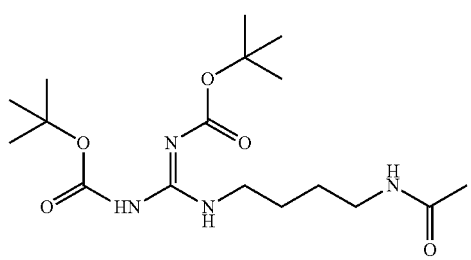 [SMILES: CC(=O)NCCCCN/C(=N\C(=O)OC(C)(C)C)NC(=O)OC(C)(C)C] | 4-(2,3-bis(tert-butyloxycarbonyl)guanidino)butylacetamide | 373.2 |
| J-5 | 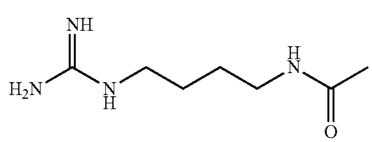 | N-(4-guanidinobutyl)acetamide | 173.1 |
| J-6 | 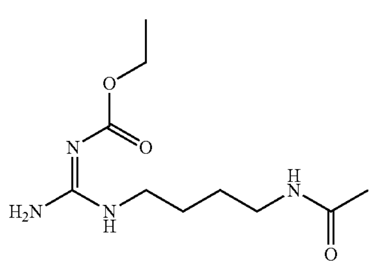 [SMILES: CCOC(=O)/N=C(/N)NCCCCNC(C)=O] | 4-(2-(ethoxycarbonyl)guanidino)butylacetamide | 245.2 |

TABLE 2-continued

Exemplary formula I compounds

| No. | Structure | IUPAC Name | Mass spec M + H |
|---|---|---|---|
| J-7 | 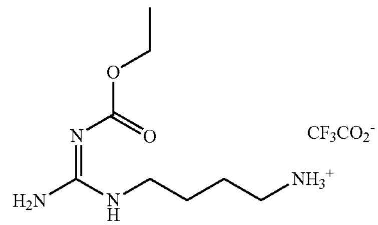 | 4-(2-(ethoxycarbonyl)guanidino)butan-1-aminium 2,2,2-trifluoroacetate | 203.2 |
| J-8 | 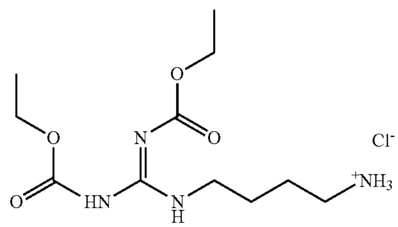 [SMILES: CCOC(=O)/N=C(\NCCCC[NH3+])NC(=O)OCC ; [Cl-]] | 4-(2,3-bis(ethoxycarbonyl)guanidino)butan-1-aminium chloride | 275.2 |
| J-9 | 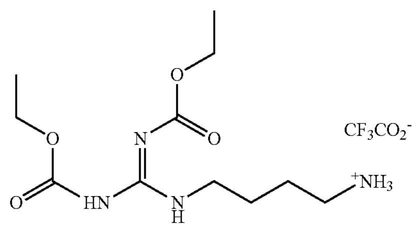 [SMILES: CCOC(=O)/N=C(\NCCCC[NH3+])NC(=O)OCC ; "CF3CO2-"] | 4-(2,3-bis(ethoxycarbonyl)guanidino)butan-1-aminium 2,2,2-trifluoroacetate | 275.2 |
| J-10 | 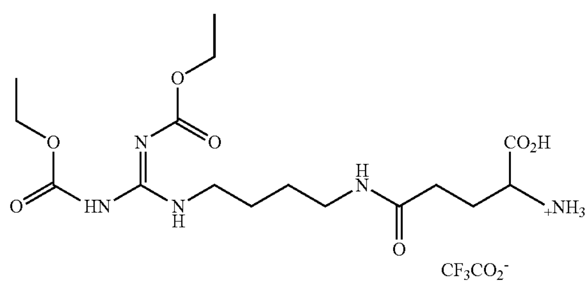 | 16-carboxy-6-((ethoxycarbonyl)amino)-4,13-dioxo-3-oxa-5,7,12-triazahexadec-5-en-16-aminium 2,2,2-trifluoroacetate | 404.2 |
| J-11 | 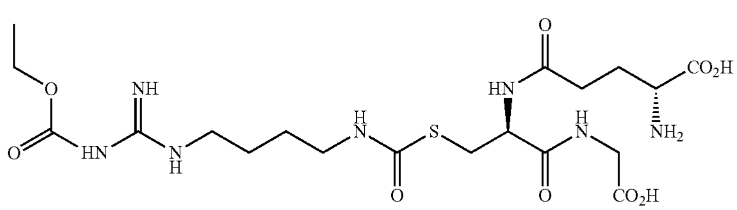 [SMILES: CCOC(=O)NC(=N)NCCCCNC(=O)SC[C@@H](NC(=O)CC[C@@H](N)C(=O)O)C(=O)NCC(=O)O] | (16S,21R)-21-amino-16-((carboxymethyl)carbamoyl)-6-imino-4,13,18-trioxo-3-oxa-14-thia-5,7,12,17-tetraazadocosan-22-oic acid | 536.2 |
| J-12 | 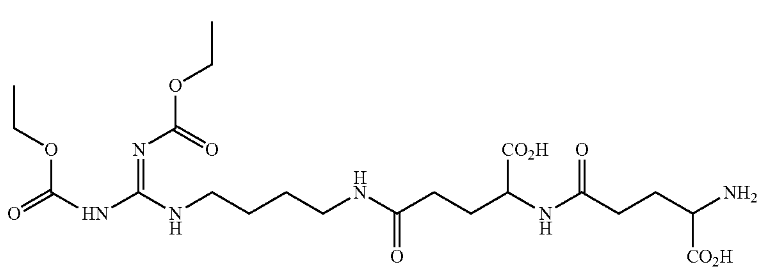 [SMILES: CCOC(=O)/N=C(\NCCCCNC(=O)CCC(NC(=O)CCC(N)C(=O)O)C(=O)O)NC(=O)OCC] | 21-amino-16-carboxy-6-((ethoxycarbonyl)amino)-4,13,18-trioxo-3-oxa-5,7,12,17-tetraazadocos-5-en-22-oic acid | 533.3 |

TABLE 2-continued

Exemplary formula I compounds

| No. | Structure | IUPAC Name | Mass spec M + H |
|---|---|---|---|
| J-13 | [structure] | 6-imino-4,13-dioxo-3-oxa-5,7,12-triazatetracosane | 399.3 |

Biological Evaluation

Without limiting the invention to any particular mechanism of action or utility, the compounds of formula I are designed to improve distribution of agmatine from the systemic circulation to the central nervous system and utilizing the following properties:
(a) Lipophilic agmatine analogs that can enter the brain by passive diffusion and release agmatine therein by the action of brain esterases;
(b) γ (gamma)-Glutamylated and doubly γ-glutamylated agmatine and analogs that capitalize on the abundance of the enzyme, γ-glutamyl transpeptidase (GGT), in the choroid plexus where agmatine and the SSAs (Strategically Substituted Agmatines) can be liberated by cleavage of the γ-glutamyl moiety(ies).
(c) Agmatine analogs linked by a carbonyl group to the sulfur of glutathione that utilize the transport system for glutathione (GSH) and/or its S-conjugates for transport across the blood brain barrier; and
(d) Agmatine analogs with an additional long chain fatty acid that can enter the brain and be hydrolyzed enzymatically therein to agmatine.

Formula I compounds were synthesized and screened in several standard assays of CNS maladaptive neuroplasticity which are associated each pre-clinical model described herein. These models and the data reasonably predict use of formula I in treatments for opioid analgesic tolerance, neuropathic pain, and opioid analgesic addiction.

Formula I compounds may serve the goal of developing both non-opioid analgesic substances and opioid adjuvants that will limit opioid analgesic tolerance (and dose requirements), dependence, and addiction when opioid analgesic therapy remains necessary.

OPIOID ANALGESIC TOLERANCE: Agmatine has been shown to reduce the development of opioid analgesic tolerance, a well-established clinical problem. To evaluate the effects of the compounds in opioid tolerance an acute in vivo bioassay of opioid analgesic tolerance was employed. In this instance, either a large dose of the mu opioid receptor selective neuropeptide ENDO-2 is given or vehicle. When the analgesic effects are no longer evident, a second analgesic dose of ENDO-2 is given. The second analgesic dose of ENDO-2 is effective in the group pre-treated with saline, but not in the group that was pre-treated with the large dose of ENDO-2. When agmatine or when one of the SSA is given together with the large pre-treatment dose of ENDO-2, the second analgesic dose of ENDO-2 is effective. In this bioassay, agmatine and most of the SSAs prevented the development of opioid tolerance.

FIGS. 1A-I illustrates the ability of centrally (doses expressed in nmol) and systemically delivered (dose expressed in mg/kg) of agmatine (Panel A) and Formula I compounds (Panels B-I) to prevent the development of spinal opioid analgesic tolerance.

Formula I compounds from Table 2 were evaluated for their impact on the development of opioid analgesic tolerance when dosed central (intrathecally) and systemically (intraperitoneally). These are displayed in FIG. 1, panels A-I. To model opioid addiction, a spinal acute tolerance model of ENDO-2, a highly mu opioid selective tetrapeptide, and the standard warm water immersion tail flick test as a dependent measure were used. When a high dose of ENDO-2 is intrathecally injected a subsequent analgesic dose is no longer effective (30 minutes later) (Stone et al., 1997). This is a model of opioid-induced analgesic tolerance.

FIG. 1A shows a dose of ENDO-2 was given that results in an analgesic effect, SAL (first bar from left). This group of mice had previously received an intrathecal injection of saline as a control to the subjects represented by ENDO-2 (second bar from left) which had an intrathecal pre-treatment of ENDO-2. When that second group received a second injection of ENDO-2 (same dose as in the SAL group), the analgesic effect was not observed. Analgesic tolerance to ENDO-2 was, therefore, induced. However, when intrathecal agmatine is co-administered with that same tolerance-inducing pre-treatment intrathecal dose of ENDO-2, the second dose of ENDO-2 demonstrates robust analgesia. AG 4 nmol (third bar from left). The inclusion of agmatine, therefore, protected against the induction of opioid tolerance. This relationship was also true when 100 mg/kg agmatine was delivered systemically (i.p., intraperitoneal) at the same time as the initial dose of intrathecal ENDO-2 (fourth bar from left). These data are consistent with other studies demonstrating that agmatine protects against the development of opioid analgesic tolerance and formed the basis for comparisons to the formula I compounds tested in the remainder of FIGS. 1B-I.

Figure 1B:
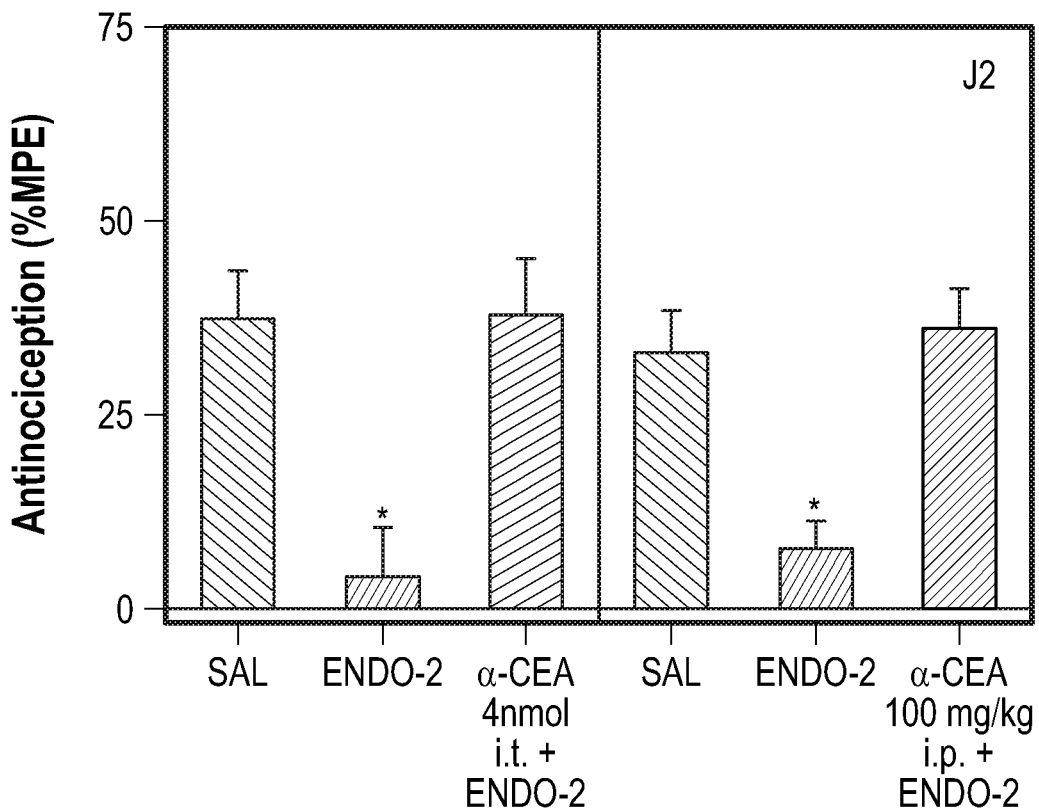
FIG. 1B shows doses of ENDO-2 were given that resulted in an analgesic effect, SAL (first bars from left) whereas pre-treatment with ENDO-2 resulted in reduced ENDO-2 analgesia, ENDO-2 (second bars from left). J-2 co-administration either intrathecally, it (third bar from left) or systemically, 100 mg/kg ip (third bar from left) prevented the development of opioid analgesic tolerance.

FIG. 1B shows doses of ENDO-2 were given that resulted in an analgesic effect, SAL (first bars from left) whereas pre-treatment with ENDO-2 resulted in reduced ENDO-2 analgesia, ENDO-2 (second bars from left). J-2 co-administration either intrathecally, it (third bar from left) or systemically, 100 mg/kg ip (third bar from left) prevented the development of opioid analgesic tolerance.

Figure 1C:
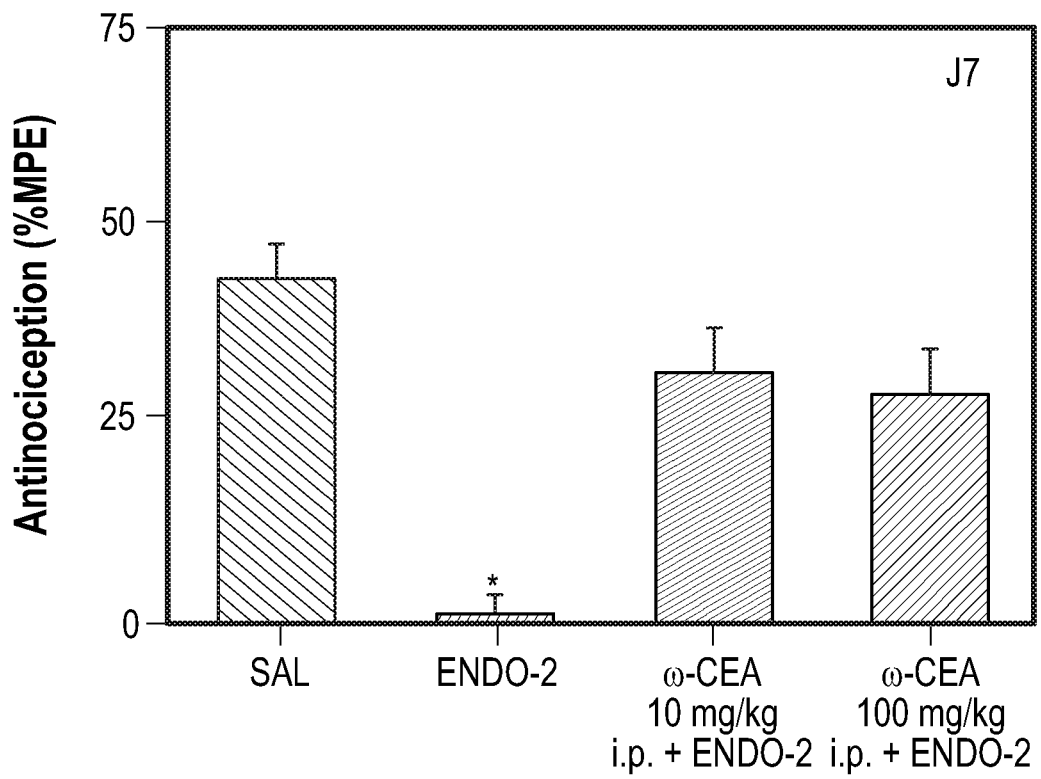
FIG. 1C shows a dose of ENDO-2 was given that resulted in an analgesic effect, SAL (first bar from left) whereas pre-treatment with ENDO-2 resulted in reduced ENDO-2 analgesia, ENDO-2 (second bar from left). Systemically delivered J-7 either at a 10 mg/kg dose, it (third bar from left) or 100 mg/kg dose, ip (fourth bar from left) prevented the development of opioid analgesic tolerance.

FIG. 1C shows a dose of ENDO-2 was given that resulted in an analgesic effect, SAL (first bar from left) whereas pre-treatment with ENDO-2 resulted in reduced ENDO-2 analgesia, ENDO-2 (second bar from left). Systemically delivered J-7 either at a 10 mg/kg dose, it (third bar from left) or 100 mg/kg dose, ip (fourth bar from left) prevented the development of opioid analgesic tolerance.

Figure 1D:
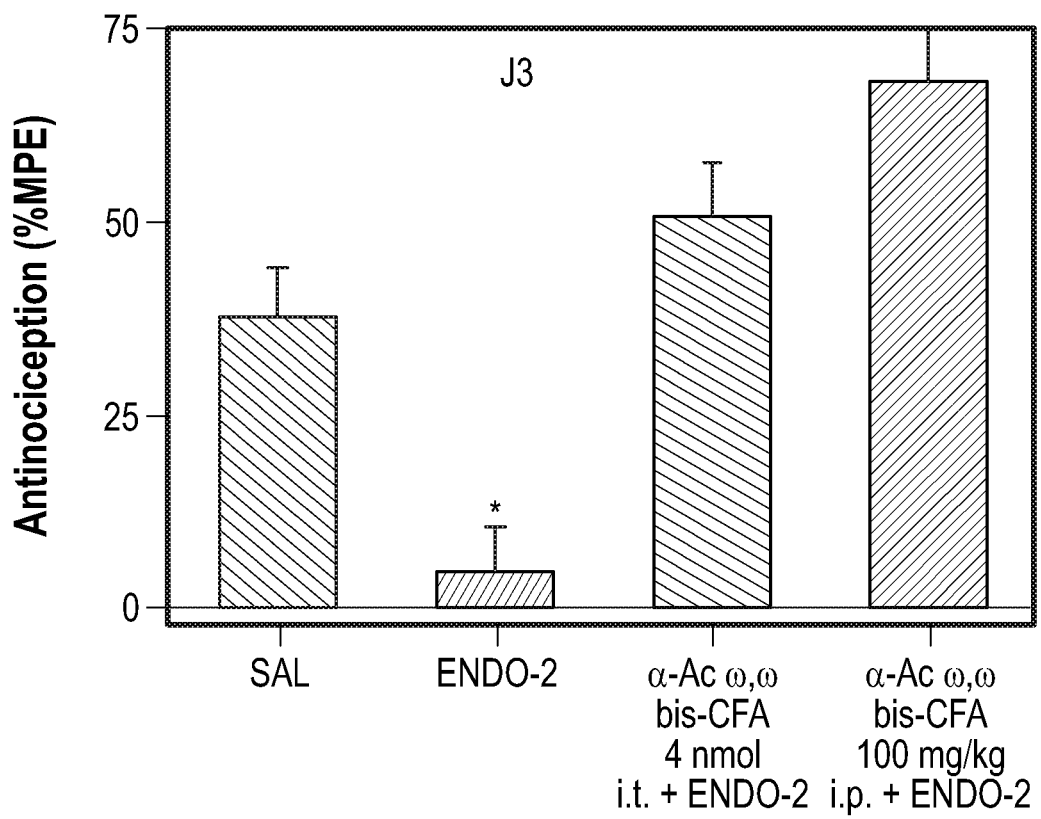
FIG. 1D shows a dose of ENDO-2 was given that resulted in an analgesic effect. SAL (first bar from left) whereas pre-treatment with ENDO-2 resulted in reduced ENDO-2 analgesia, ENDO-2 (second bar from left). J-3 co-administration either intrathecally, it (third bar from left) or systemically, ip (fourth bar from left) prevented the development of opioid analgesic tolerance.

FIG. 1D shows a dose of ENDO-2 was given that resulted in an analgesic effect, SAL (first bar from left) whereas pre-treatment with ENDO-2 resulted in reduced ENDO-2 analgesia, ENDO-2 (second bar from left). J-3 co-administration either intrathecally, it (third bar from left) or systemically, ip (fourth bar from left) prevented the development of opioid analgesic tolerance.

Figure 1E:
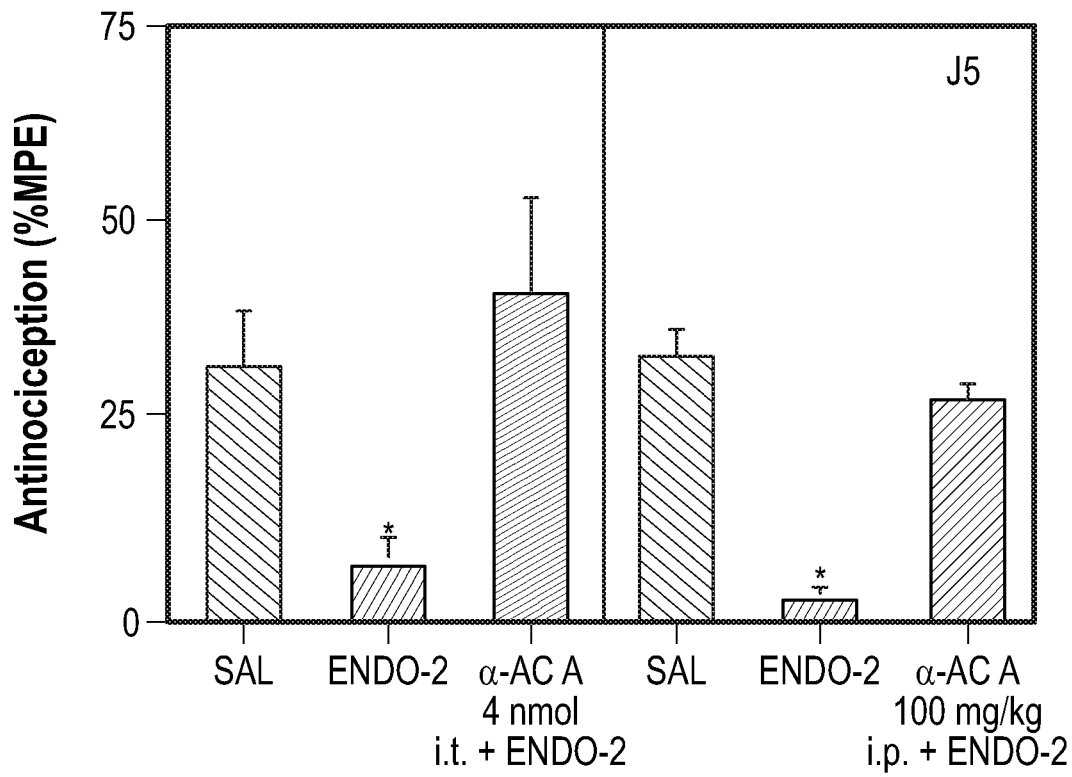
FIG. 1E shows doses of ENDO-2 were given that resulted in an analgesic effect, SAL (first bars from left) whereas pre-treatment with ENDO-2 resulted in reduced ENDO-2 analgesia, ENDO-2 (second bars from left). J-5 co-administration either intrathecally, it (third bar from left) or systemically, 100 mg/kg ip (third bar from left) prevented the development of opioid analgesic tolerance.

FIG. 1E shows doses of ENDO-2 were given that resulted in an analgesic effect, SAL (first bars from left) whereas pre-treatment with ENDO-2 resulted in reduced ENDO-2 analgesia, ENDO-2 (second bars from left). J-5 co-administration either intrathecally, it (third bar from left) or systemically, 100 mg/kg ip (third bar from left) prevented the development of opioid analgesic tolerance.

Figure 1F:
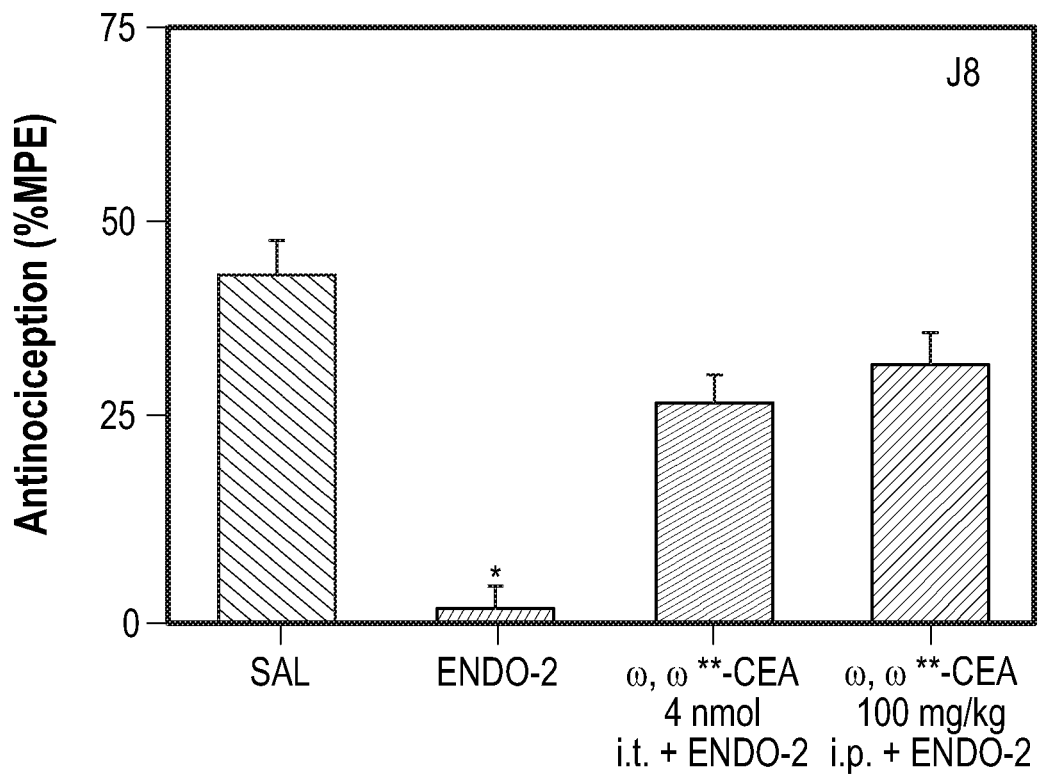
FIG. 1F shows, a dose ENDO-2 was given that resulted in an analgesic effect, SAL (first bar from left) whereas pre-treatment with ENDO-2 resulted in reduced ENDO-2 analgesia, ENDO-2 (second bar from left). J-8 delivered either intrathecally, it (third bar from left) or systemically, ip (fourth bar from left) prevented the development of opioid analgesic tolerance.

FIG. 1F shows, a dose ENDO-2 was given that resulted in an analgesic effect, SAL (first bar from left) whereas pre-treatment with ENDO-2 resulted in reduced ENDO-2 analgesia, ENDO-2 (second bar from left). J-S delivered either intrathecally, it (third bar from left) or systemically, ip (fourth bar from left) prevented the development of opioid analgesic tolerance.

Figure 1G:
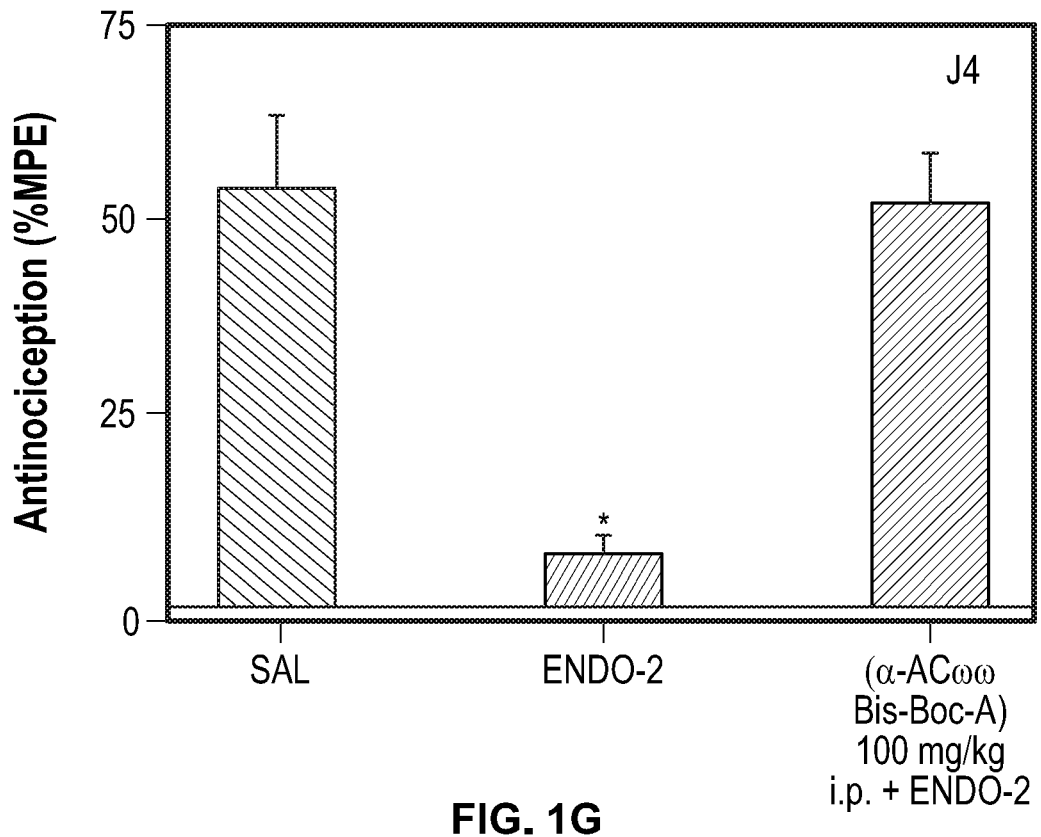
FIG. 1G shows a dose of ENDO-2 was given that resulted in an analgesic effect. SAL (first bar from left) whereas pre-treatment with ENDO-2 resulted in reduced ENDO-2 analgesia, ENDO-2 (second bar from left). J-4 delivered systemically, ip (third bar from left) prevented the development of opioid analgesic tolerance.

FIG. 1G shows a dose of ENDO-2 was given that resulted in an analgesic effect. SAL (first bar from left) whereas pre-treatment with ENDO-2 resulted in reduced ENDO-2 analgesia, ENDO-2 (second bar from left). J-4 delivered systemically, ip (third bar from left) prevented the development of opioid analgesic tolerance.

Figure 1H:
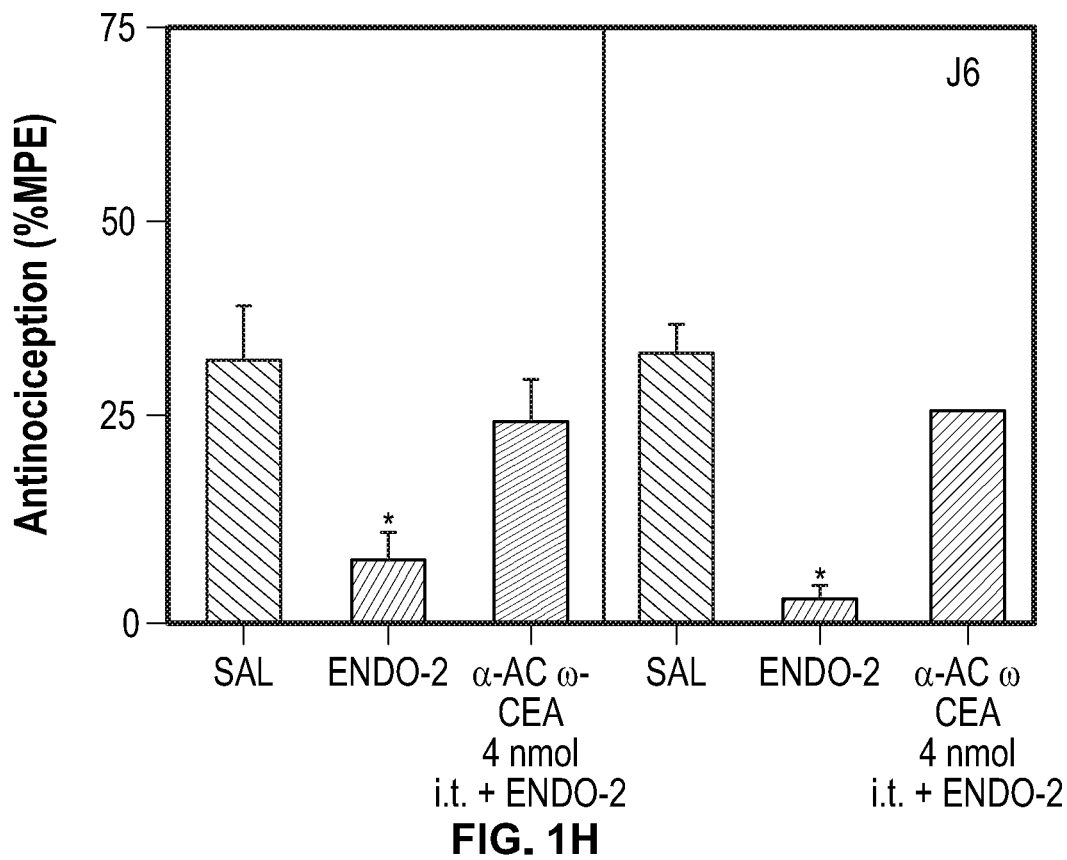
FIG. 1H shows doses of ENDO-2 were given that resulted in an analgesic effect, SAL (first bars from left) whereas pre-treatment with ENDO-2 resulted in reduced ENDO-2 analgesia, ENDO-2 (second bars from left). J-6 co-administration either intrathecally, it (third bar from left) or systemically, 100 mg/kg ip (third bar from left) prevented the development of opioid analgesic tolerance.

FIG. 1H shows doses of ENDO-2 were given that resulted in an analgesic effect, SAL (first bars from left) whereas pre-treatment with ENDO-2 resulted in reduced ENDO-2 analgesia, ENDO-2 (second bars from left). J-6 co-administration either intrathecally, it (third bar from left) or systemically, 100 mg/kg ip (third bar from left) prevented the development of opioid analgesic tolerance.

Figure 1I:
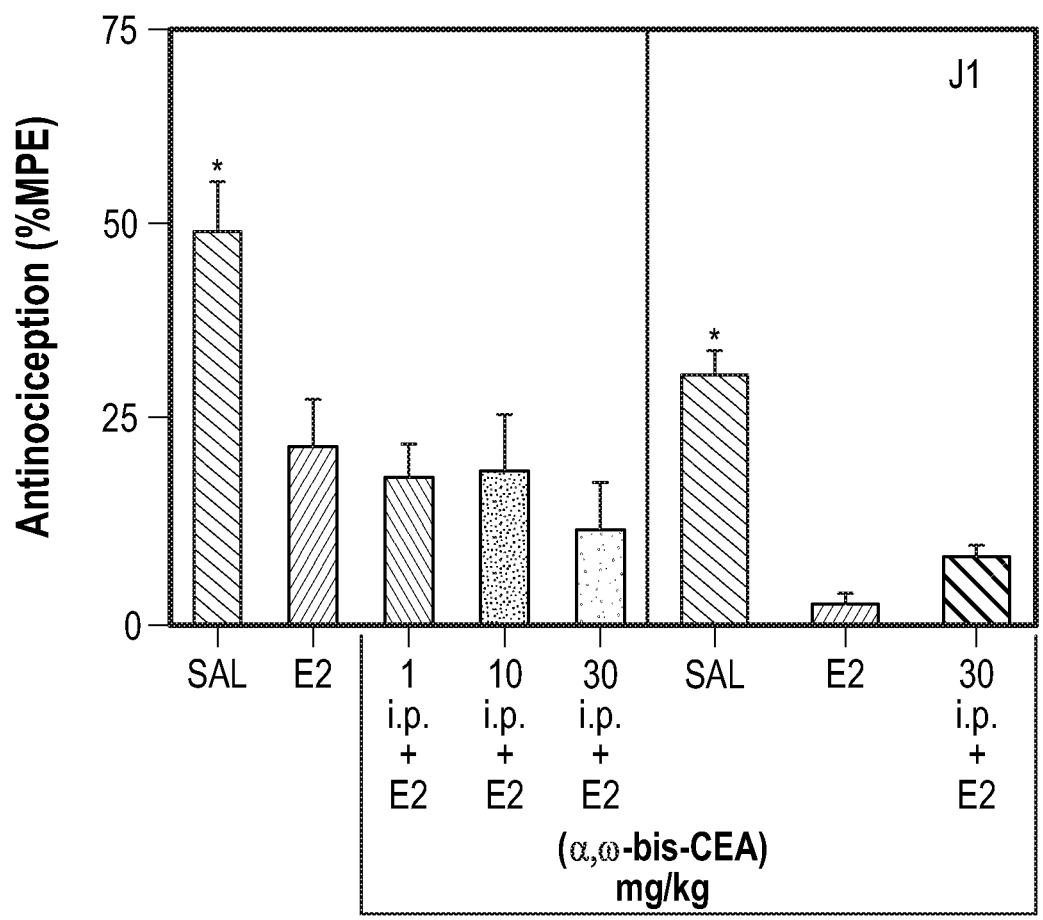
FIG. 1I shows doses of ENDO-2 were given that resulted in an analgesic effect, SAL (first bars from left) whereas pre-treatment with ENDO-2 resulted in reduced ENDO-2 analgesia, E2 (second bars from left). J-1 co-administration either systemically at a dose range of 1-30 mg/kg (third, fourth, fifth bars from left) did not prevent the development of opioid analgesic tolerance.

FIG. 1I shows doses of ENDO-2 were given that resulted in an analgesic effect, SAL (first bars from left) whereas pre-treatment with ENDO-2 resulted in reduced ENDO-2 analgesia, E2 (second bars from left). J-1 co-administration either systemically at a dose range of 1-30 mg/kg (third, fourth, fifth bars from left) did not prevent the development of opioid analgesic tolerance.

These data show that, in most cases, the formula I compounds J-(1-13) of Table 2 prevent the development of opioid analgesic tolerance when given either intrathecally or systemically, demonstrating these new chemical entities may be effective co-adjuvants for opioid analgesics.

Figure 7A:
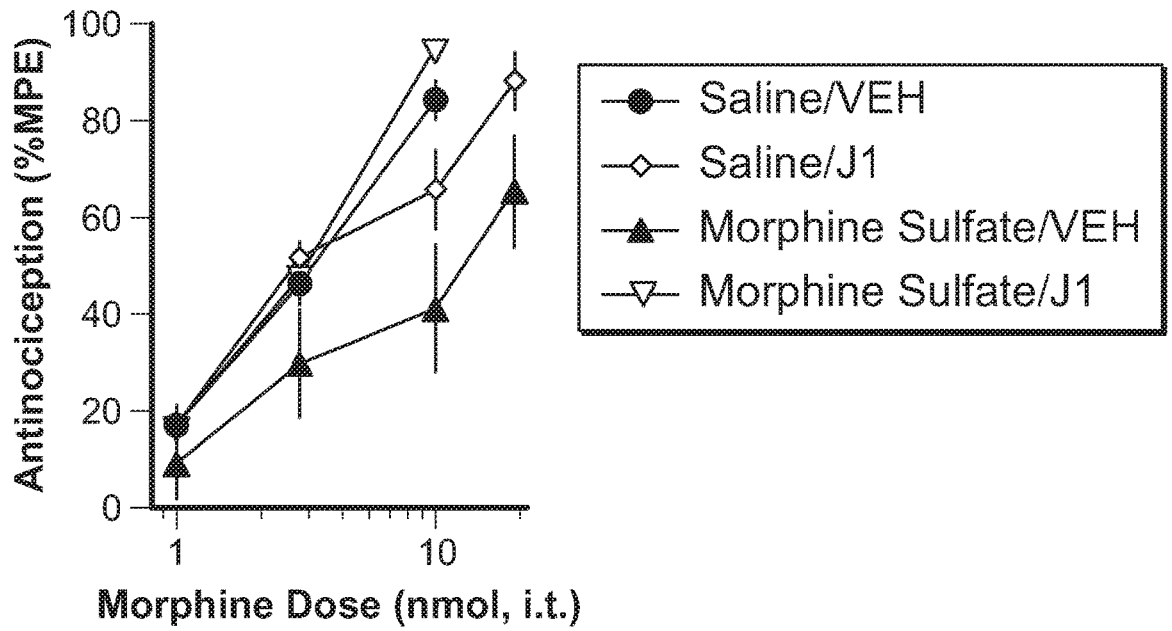
FIG. 7A shows the ability of intrathecally administered compound J-1 to block the development of tolerance to intrathecally delivered morphine. Mice received morphine (10 nmol, i.t.) or vehicle concurrently with compound J-1 (10 nmol, i.t.) b.i.d for 3 days. On day 4, four cumulative doses of morphine were given intrathecally to assess tolerance in the warm water tail flick test.
Figure 7B:
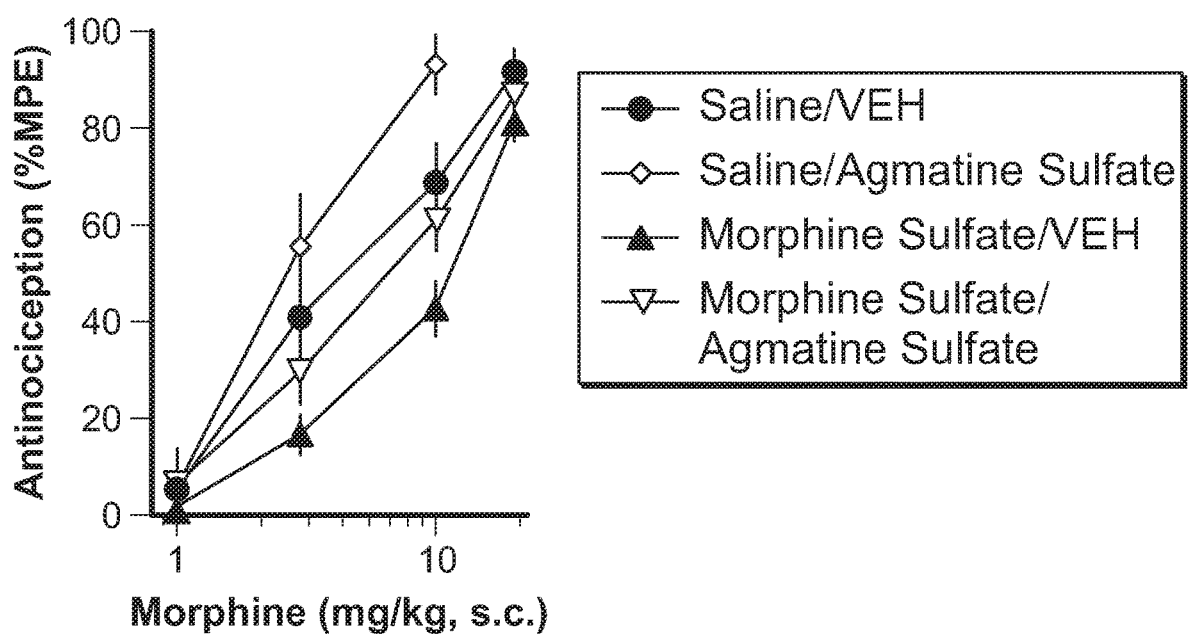
FIG. 7B shows the ability of systemically administered agmatine to block the development of tolerance to systemically delivered morphine in mice.
Figure 7C:
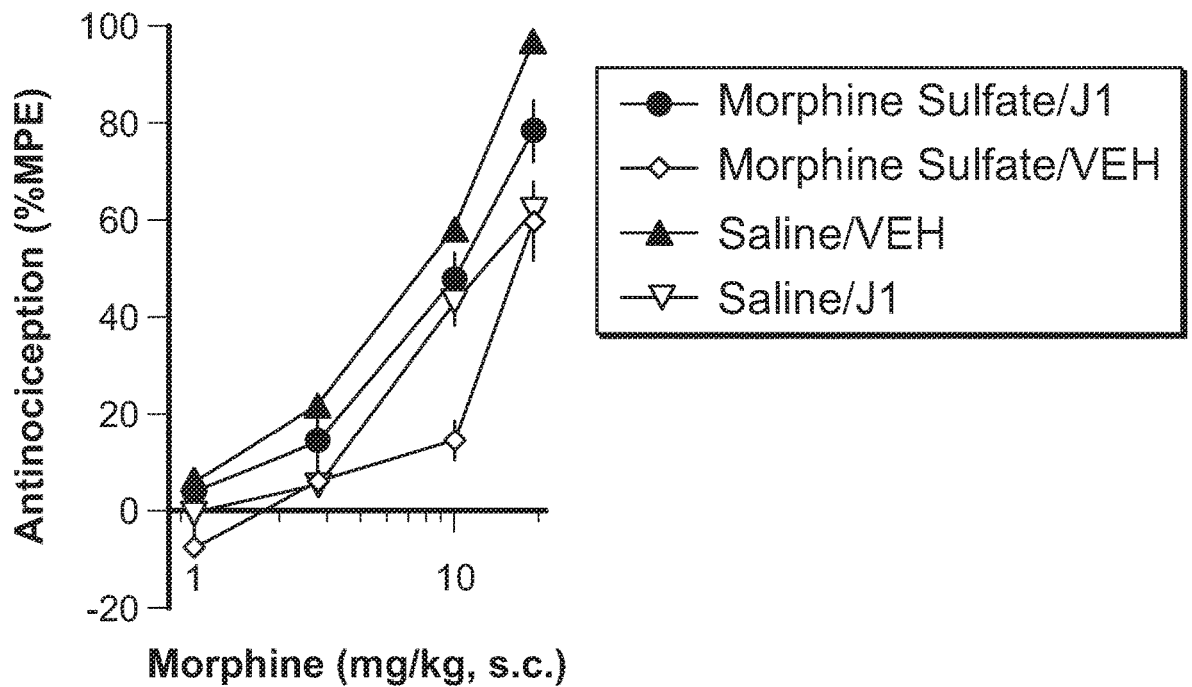
FIG. 7C shows the ability of systemically administered compound J-1 to block the development of tolerance to systemically delivered morphine in mice.
Figure 7D:
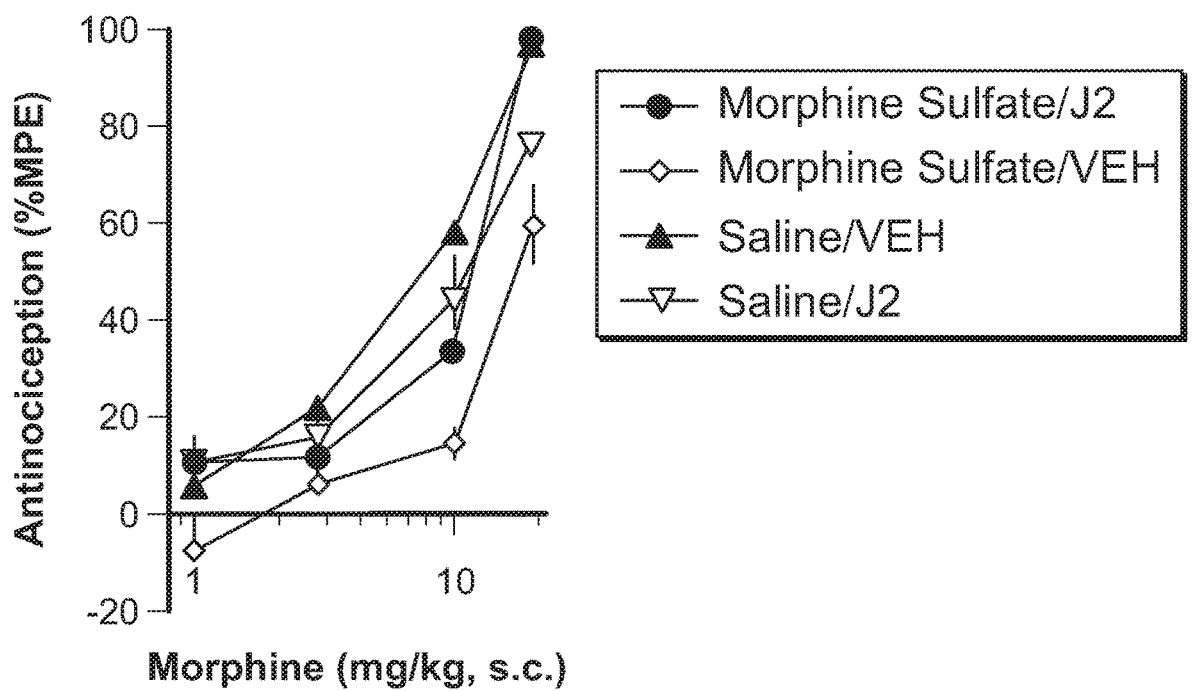
FIG. 7D shows the of compound J-2 to block the development of tolerance to systemically delivered morphine in mice.

FIG. 7A shows that repeated doses of intrathecally delivered morphine results in analgesic tolerance to subsequently delivered intrathecal morphine. Co-administration of intrathecally delivered J-1 with morphine prevented the development of central morphine tolerance. FIGS. 7B-D shows that systemically delivered morphine resulted in analgesic tolerance to subsequently systemically delivered morphine. Co-administration of either systemically delivered agmatine (FIG. 7B) or J-1. (FIG. 7C) or J-2 (FIG. 7D) reduces or prevents the development of systemic morphine tolerance.

For the experiments of FIGS. 7A-D, mice received morphine (10 mg/kg, s.c.) or vehicle concurrently with agmatine (3 mg/kg s.c.), compound J-1 (3 mg/kg, s.c.), compound J-2 (3 mg/kg, s.c.) or vehicle. Doses were administered t.i.d. every 8 hours for 4 days. On day 6, four cumulative doses of morphine were given subcutaneously to assess tolerance in the warm water (52° C.) tail flick test. In all cases, the right-most dose-response curve (morphine+vehicle) shows the development of morphine tolerance, whereas agmatine or compounds J-1 or J-2 reduced or prevented the development of tolerance (Tables 1A and 1B). The $ED_{50}$ values in Tables 1A and 1B are specific for these proof-of-concept studies of FIGS. 7A-D and may show variability under other conditions.

TABLE 1A

Effect of intrathecal J-1 on the development of central morphine tolerance

| Treatment | $ED_{50}$ (nmol, i.t.) |
| --- | --- |
| Saline/VEH | 3.21 (2.71, 3.79) |
| Saline/J-1 | 3.82 (2.95, 4.94) |
| Morphine/VEH | 10.84 (4.94, 23.82) |
| Morphine/J-1 | 2.86 (2.41, 3.40) |

TABLE 1B

Effect of systemic agmatine, J-1 or J-2 on the development of chronic morphine tolerance

| Treatment | $ED_{50}$ (95% CI) (mg/kg, s.c.) |
| --- | --- |
| Saline/VEH | 5.67 (4.98, 6.45) |
| Saline/Agmatine | 2.98 (2.27, 3.90) |
| Saline/J-1 | 13.89 (10.68, 18.05) |
| Saline/J-2 | 9.17 (6.70, 12.55) |
| Morphine/VEH | 24.95 (14.34, 43.41) |
| Morphine/Agmatine | 5.74 (4.59, 7.16) |
| Morphine/J-1 | 8.67 (6.67, 11.26) |
| Morphine/J-2 | 7.73 (5.63, 10.62) |

NEUROPATHIC PAIN. Formula I compounds were used to study their effects in a mouse model of spinal nerve injury-induced neuropathic pain. These experiments in mice have shown that several of these compounds when delivered intravenously at a dose of 1.35 micromoles/kg reduces established neuropathic pain with either equivalent or greater efficacy or potency than agmatine delivered intravenously at the same dose. Attached is a summary of these pharmacological outcomes (FIGS. 2-5). These data provide proof-of-concept that formula I compounds may provide control of chronic neuropathic pain at a lower potency and/or greater onset than the parent compound, agmatine.

Figure 2A:
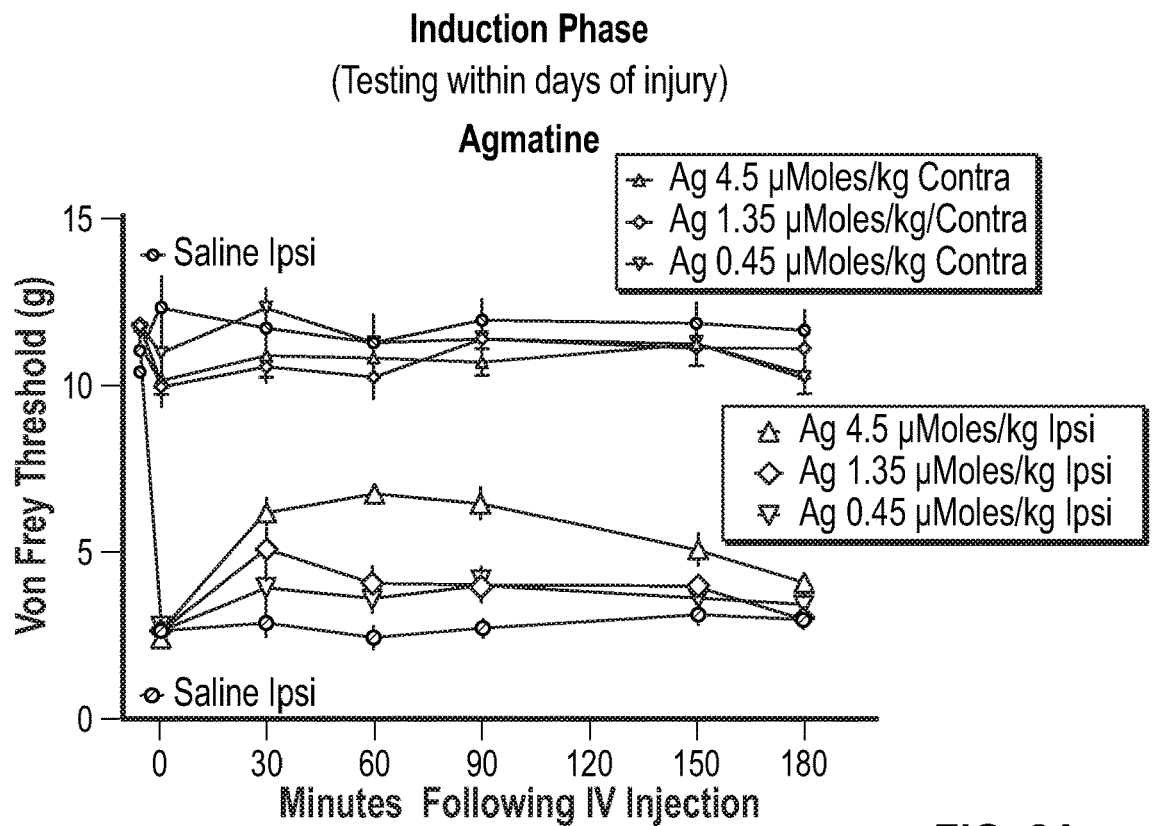
FIGS. 2A-F show pharmacological assessments of agmatine and formula I compounds from Table 2 in mice with chronic pain induced by nerve-injury. Analgesic assessment was made with the full dose-response and duration of action analyses featured for intravenously delivered agmatine (FIGS. 2A and 2B), J-3 (FIGS. 2C and 2D) and J-4 (FIGS. 2E and 2F).
Figure 2B:
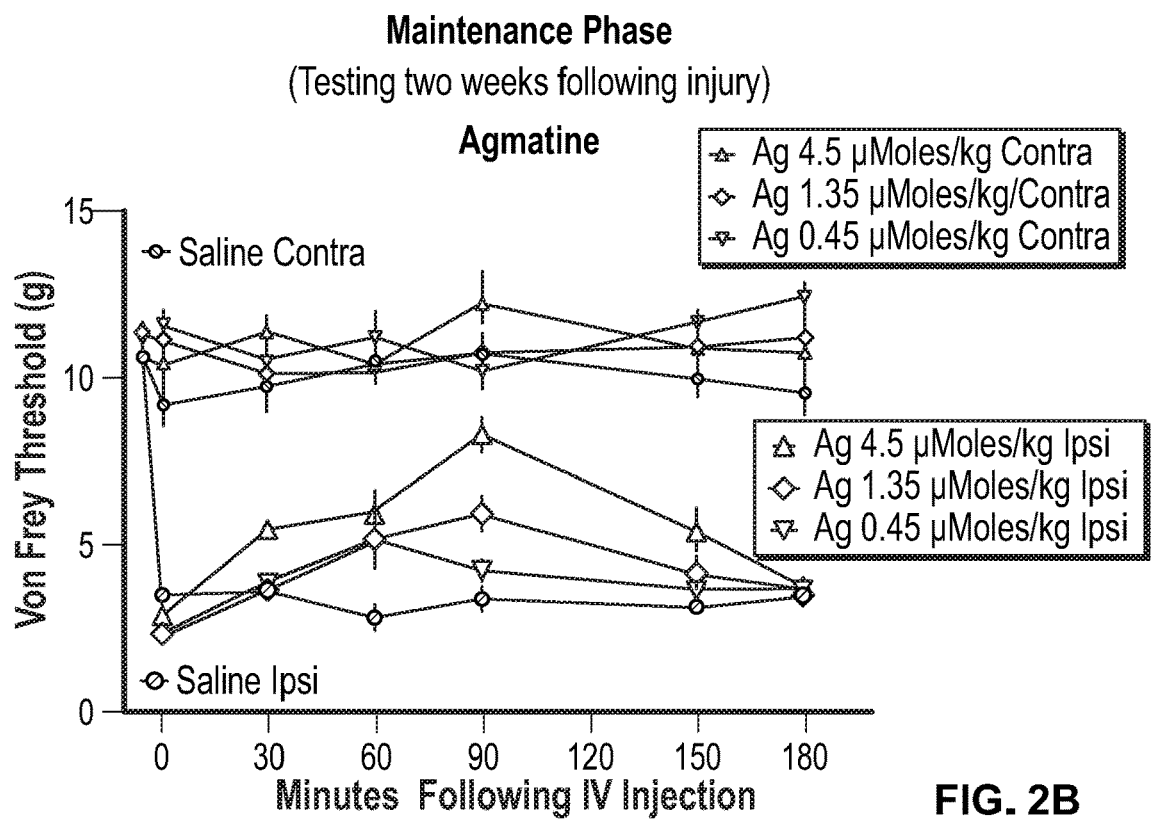
Figure 2C:
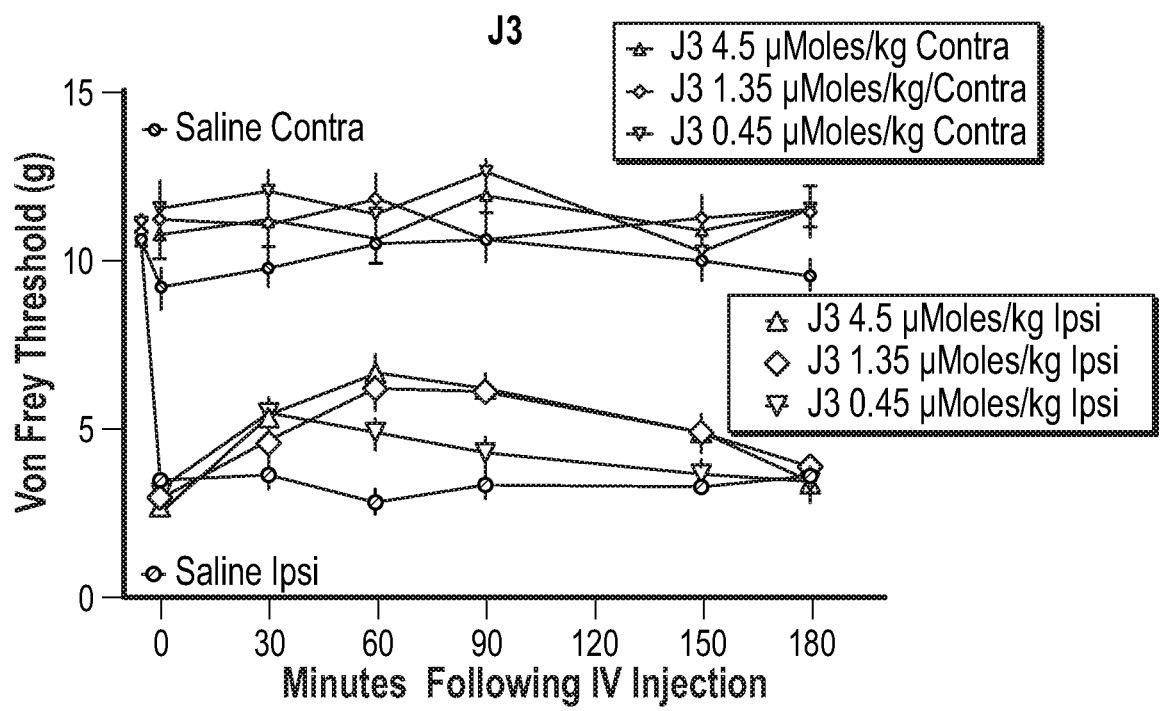
Figure 2D:
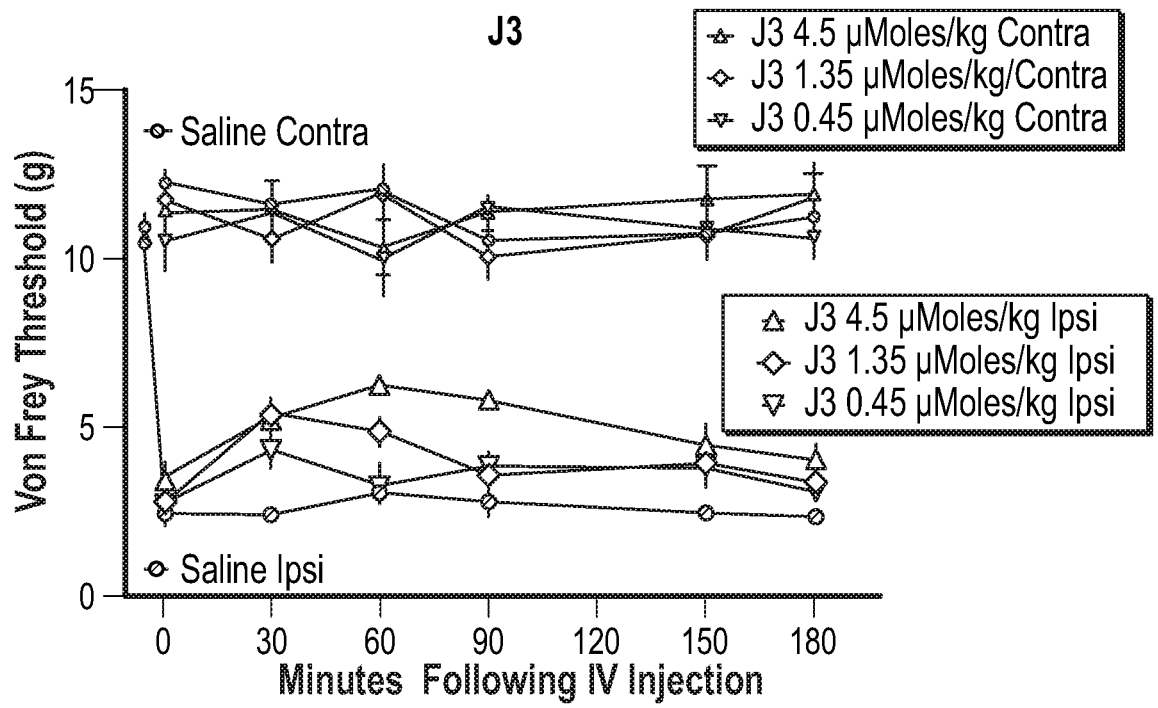
Figure 2E:
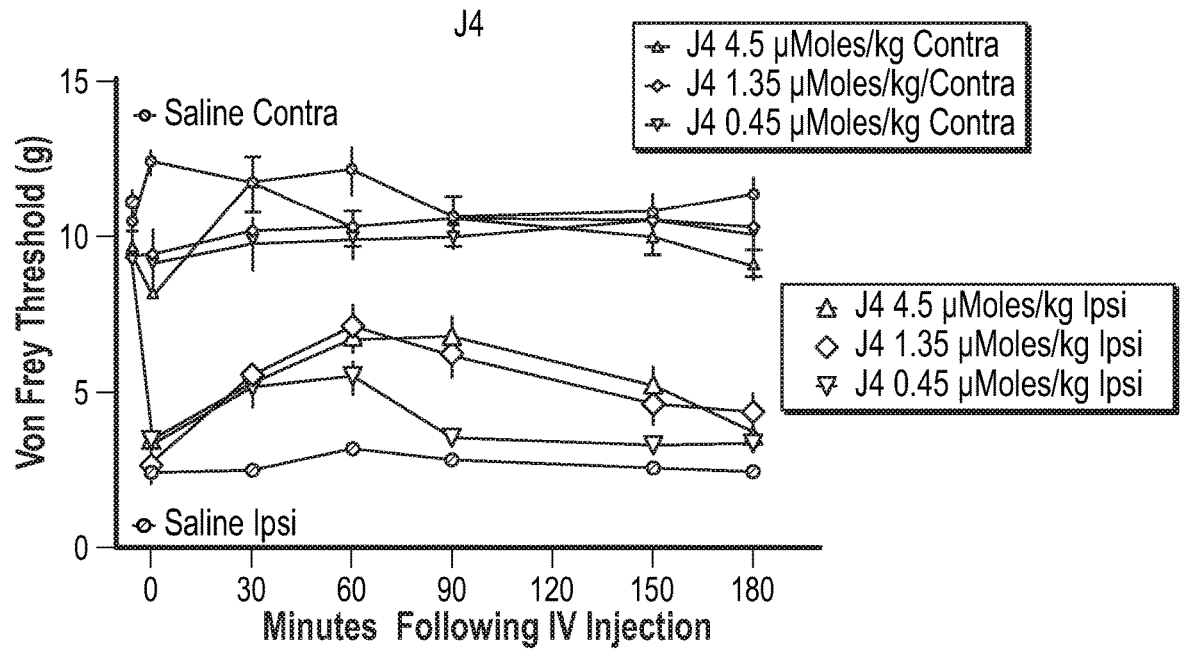
Figure 2F:
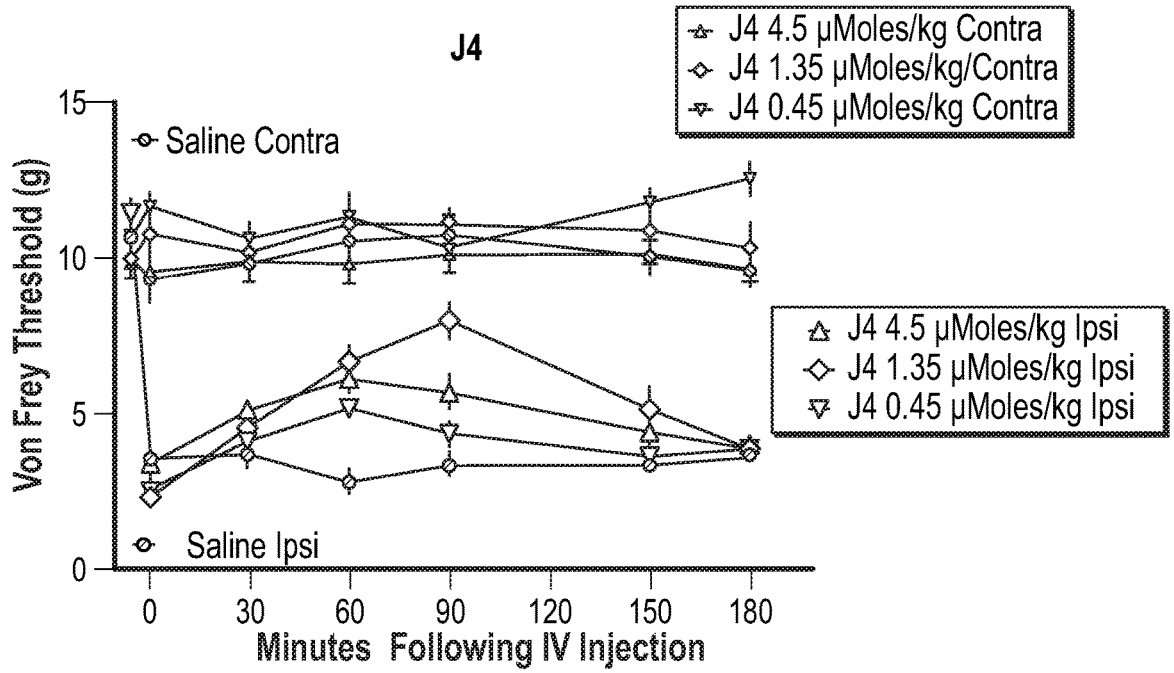

Effectiveness of Strategically Substituted Agmatines (SSAs) in Neuropathic Pain. Analgesic Assessment. The full dose-response and duration of action analyses are featured below for intravenously delivered agmatine (FIGS. 2A and 2B), and two formula I compounds from Table 2, J-3 (FIGS. 2C and 2D) and J-4 (FIGS. 2E and 2F). It is noteworthy that the magnitude of effect is nearly comparable to that seen with morphine in this same model (data not shown). FIGS. 2A, 2C, and 2E represent studies that took place during the INDUCTION phase of chronic pain, within the first week after surgery to induce nerve-injury. FIGS. 2B, 2D, and 2F represent studies that took place during the MAINTENANCE phase of chronic pain, two weeks after surgery to induce nerve-injury. For each drug three doses were administered (0.45, 1.35, 4.5 micromoles/kg). The doses were delivered sequentially low dose, moderate, high dose on separate days of study. The sensory assessment used was the von Frey monofilament tactile hypersensitivity approach. Thresholds were above ten grams prior to surgery. Following surgery, the hindpaws ipsilateral to the injury (ipsi) withdrew their hindpaws at significantly lower levels of force. Following IV administration of agmatine, J-3, J-4, but not saline (circles), the hindpaw withdrawal thresholds elevated toward control levels of responding (represented by the responses of the hindpaws contralateral to the injury (contra). No significant difference was seen with J-3 compared to the response of agmatine. However, the response of J-4 at the 1.35 micromole dose (FIG. 2F) is distinctly greater than that of agmatine at the same dose (FIG. 2B).

Figure 3A:
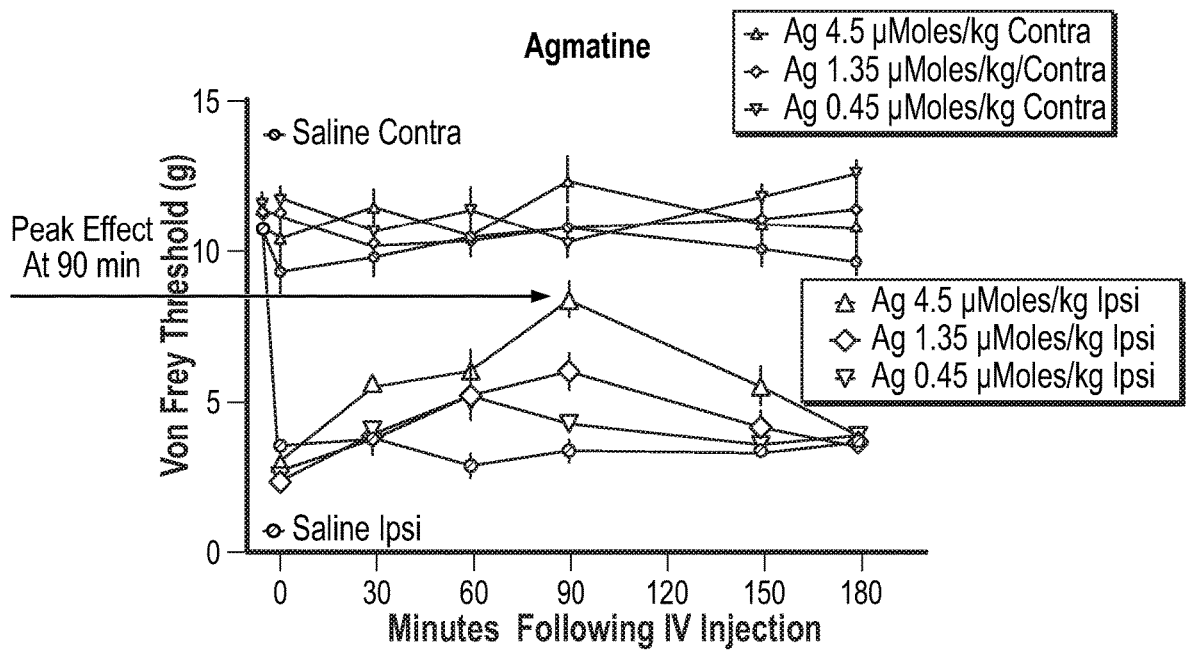
FIGS. 3A and 3B show pharmacological assessments of agmatine and the J-1 compound from Table 2 in mice with chronic pain induced by nerve-injury. The J-1 compound showed a significantly earlier time to onset of effect (FIG. 3B) compared to agmatine (FIG. 3A).
Figure 3B:
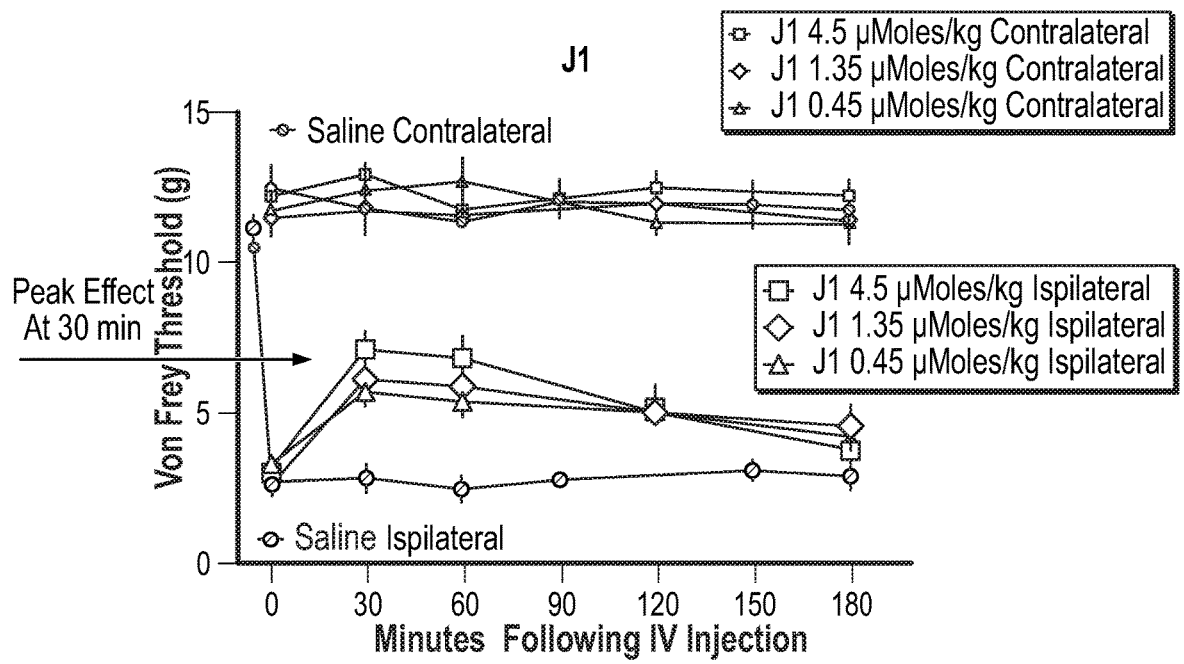

FIG. 3 shows a pharmacological assessment of agmatine and the J-1 compound from Table 2 in mice with chronic pain induced by nerve-injury. The J-1 compound showed a significantly earlier time to onset of effect (FIG. 3B) compared to agmatine (FIG. 3A).

Behavioral Toxicity: Lack of Side Effects of Formula I Compounds

Figure 4A:
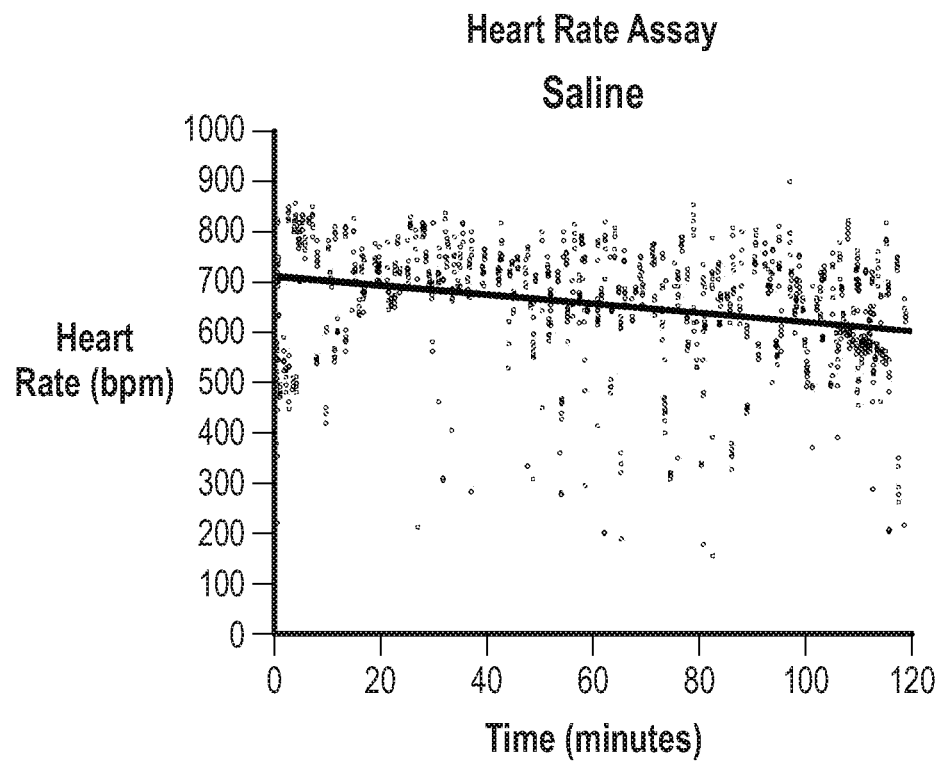
FIGS. 4A, 4C, 4D, and 4E show the impact on heart rate of i.v. injection of Saline (FIG. 4A), Agmatine (FIG. 4C), Clonidine (FIG. 4D) and J-4 (FIG. 4E).
Figure 4B:
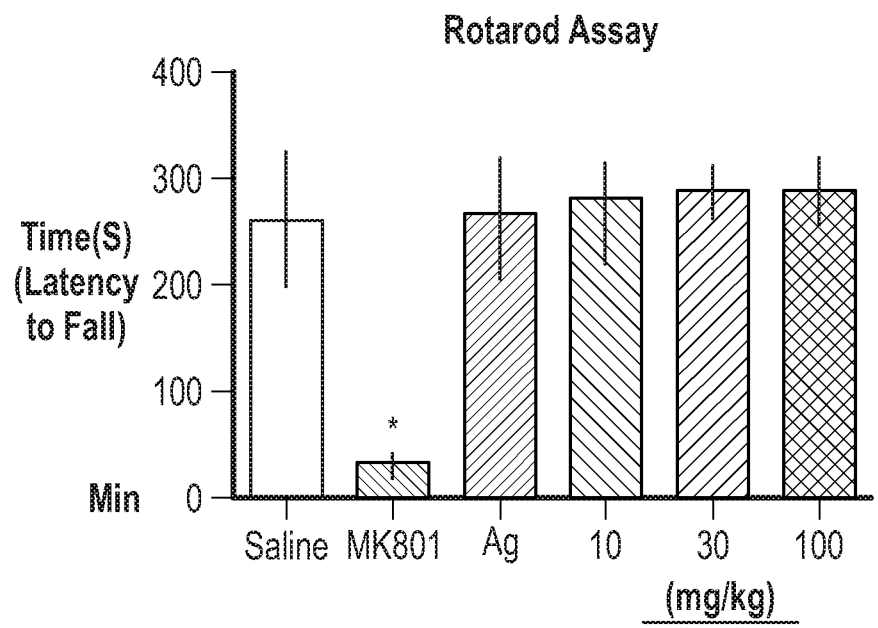
FIG. 4B shows the Rotarod assay of motor dysfunction and sedation.
Figure 4C:
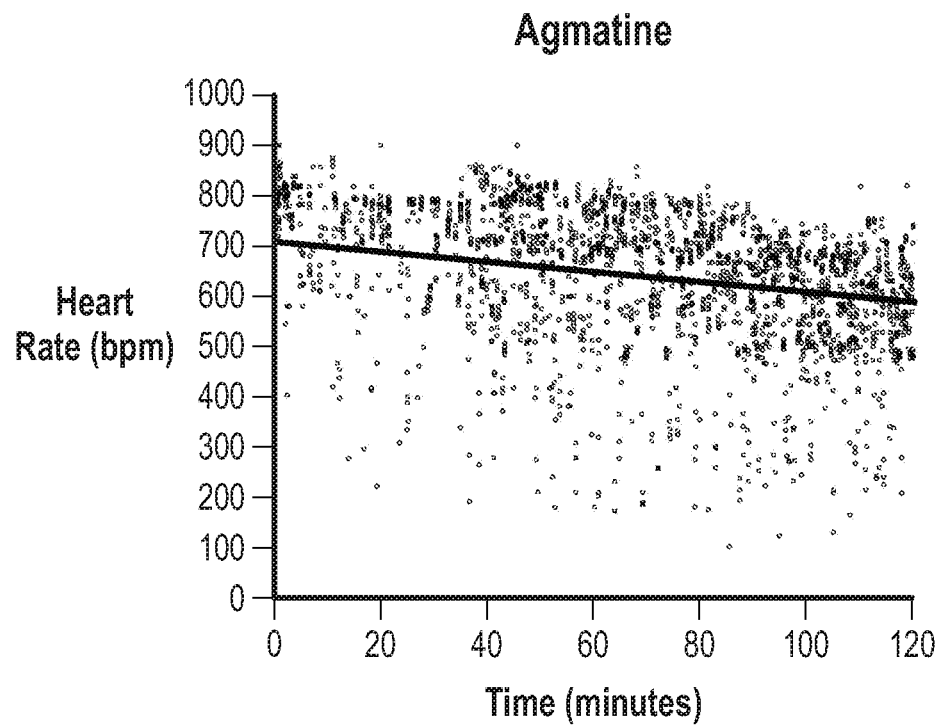
Figure 4D:
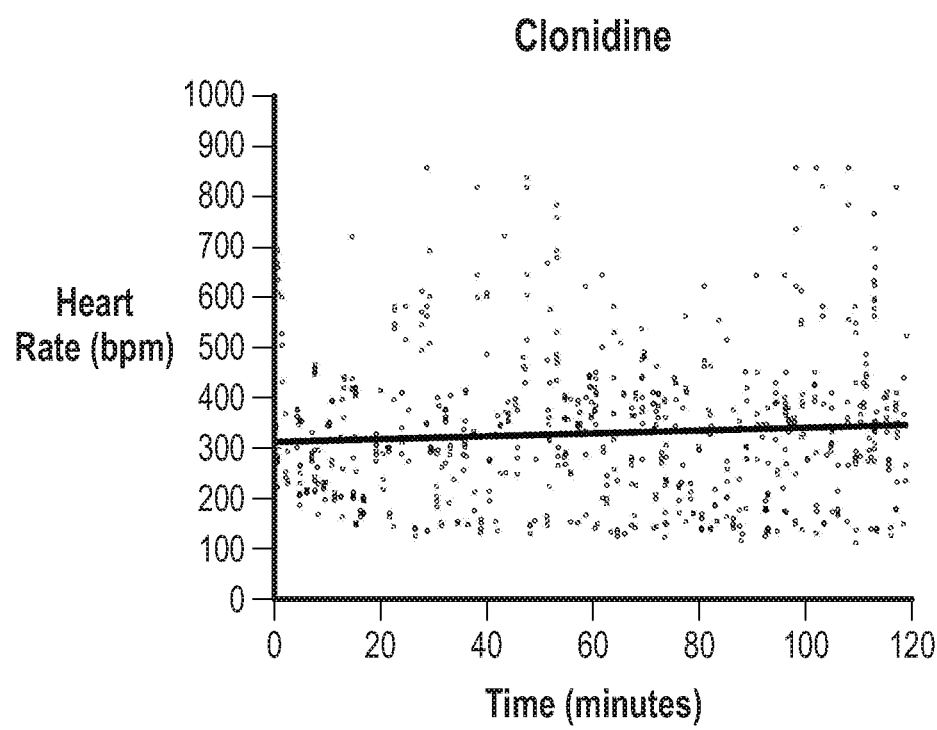
Figure 4E:
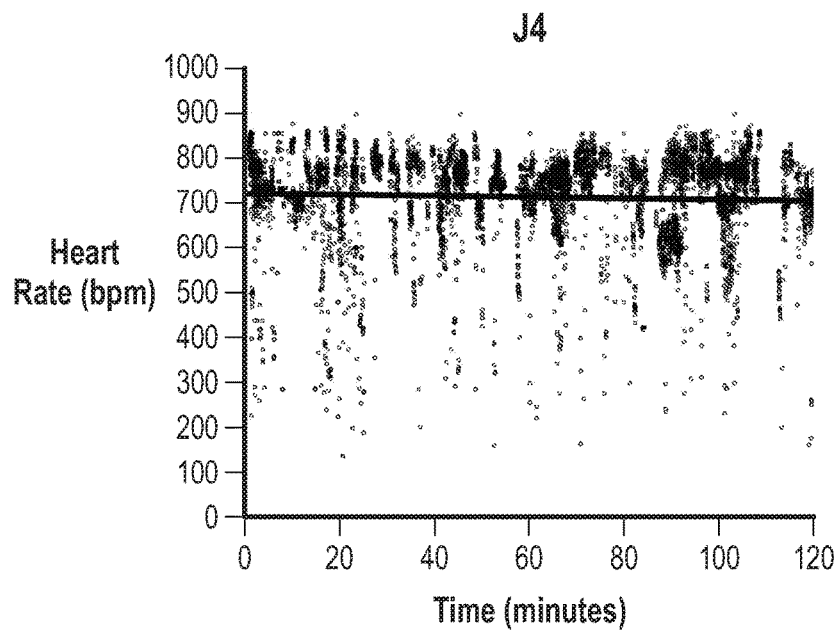

Side effects common to NMDA receptor antagonists and NOS inhibitors were assessed with the formula I compounds J-3 and J-4 of Table 2. Agmatine and J-3 and J-4 compounds were found to have no impact on cardiovascular measures. Featured in FIG. 4 is the impact on heart rate of i.v. injection of Saline (FIG. 4A), Agmatine (FIG. 4C), Clonidine (FIG. 4D) and J-4 (FIG. 4E). As expected, the alpha2 adrenergic receptor clonidine reduced heart rate for 60 minutes post-injection, but neither agmatine or J-4 had any effect. None of the formula I compounds demonstrated any effect. A full dose-response analysis of agmatine and J-3 and J-4 in the rotarod assay of motor dysfunction and sedation (FIG. 4B) was conducted. NMDA receptor antagonists are commonly known to result in motor dysfunction and the NMDA receptor antagonists are known to impact the performance of rodents in the rotarod assay. It has been previously observed that, unlike other NMDA receptor antagonists such as MK801, intrathecal agmatine does not impact rotarod performance in mice. Consistently, intravenously administered agmatine did not impact rotarod performance nor did J-3 nor did J-4 at doses that were effective in reducing vF thresholds in nerve-injured mice. FIG. 4B features rotarod performance of nerve-injured mice that were intravenously injected with either saline, MK801, agmatine or increasing doses of J-4 and tested on rotarod at 30 minutes post-injection. Formula I compounds do not demonstrate any negative impact on assays of rotarod performance or cardiovascular function.

Figure 5:
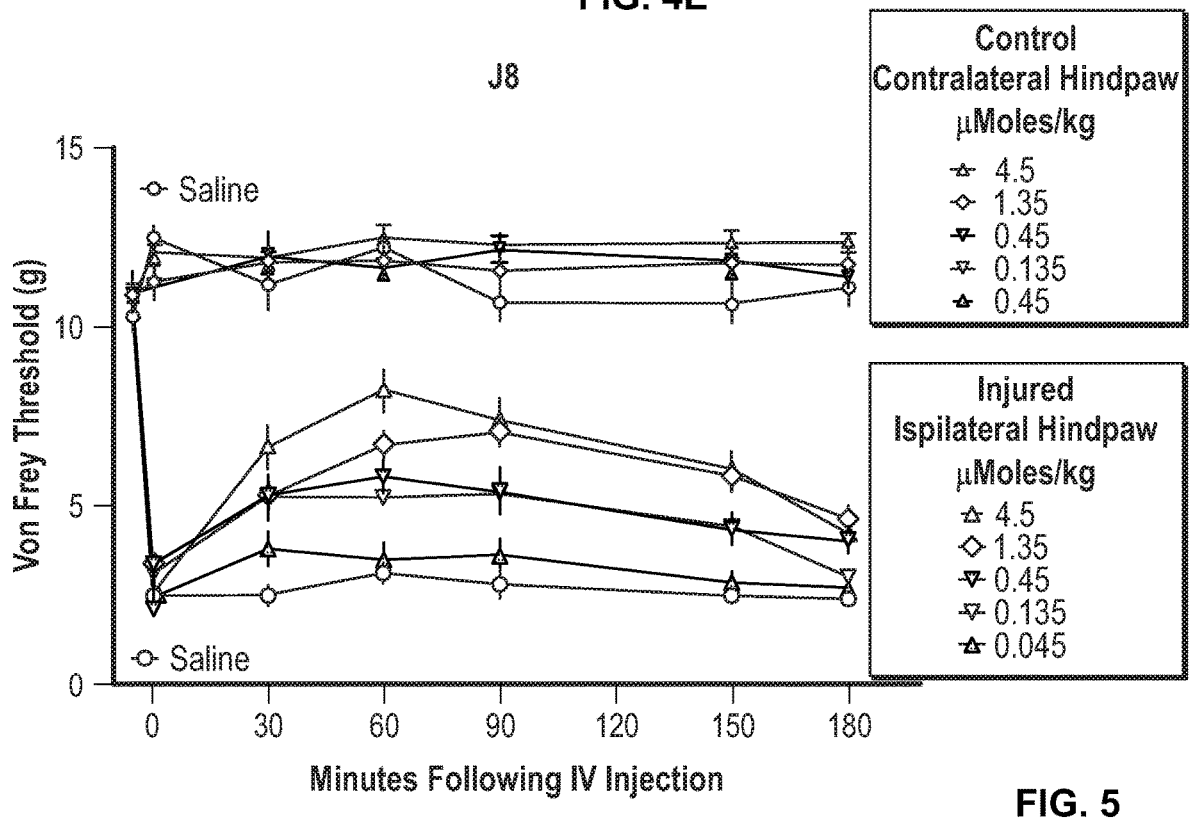
FIG. 5 shows the full dose-response and duration of action analyses for intravenously delivered formula I compound J-8 from Table 2.

The full dose-response and duration of action were assessed for an intravenously delivered formula I compound J-8 (FIG. 5). The study was conducted during the Induction phase of chronic pain, within the first week after surgery to induce nerve-injury. Five doses were administered (0.045, 0.0135, 0.45, 1.35, 4.5 micromoles/kg) which correspond to approximately 1, 3, 10, 30, and 100 mg/kg. The doses were delivered in the following order 30, 10, 3, 1, 100 mg/kg on separate days of study. An example of responses of subjects to vehicle (saline) injection from a previous study is provided as a reference point. The sensory assessment used was the von Frey monofilament tactile hypersensitivity approach. Thresholds were above ten grams prior to surgery. Following surgery, the hindpaws ipsilateral to the injury (ipsi) withdrew their hindpaws at significantly lower levels of force whereas the responses of the uninjured or contralateral hindpaws maintained their responding at baseline levels throughout the testing period. These are represented in FIG. 5 as controls to the responses of the injured paws. Following IV administration of J-8, but not saline (circles), the hindpaw withdrawal thresholds elevated significantly toward control levels of responding in a dose-dependent manner. Modification of agmatine by certain functional groups, such as ethoxycarbonyl on the guanine may facilitate crossing of the blood brain barrier to enter the central nervous system. The functional data presented here are congruent with such a proposal and support the central hypothesis. Early side effects studies indicate no impact of J-8 on motor impairment or on cardiovascular measures.

OPIOID ADDICTION: In addition to evaluating formula I compounds in models of opioid analgesic tolerance and neuropathic pain; the effects of formula I compounds were assessed in a model of opioid addiction. It has been previously shown that agmatine diminishes heroin-induced self-administration in rats (Morgan A. D. et al., *Pharmacology, Biochemistry, and Behavior* (2002) 72: 873-80) and oral fentanyl self-administration in mice (Wade, C. L., et al., *Eur J Pharmacol*, (2008) 587(1-3): p. 135-40).

Figure 6A:
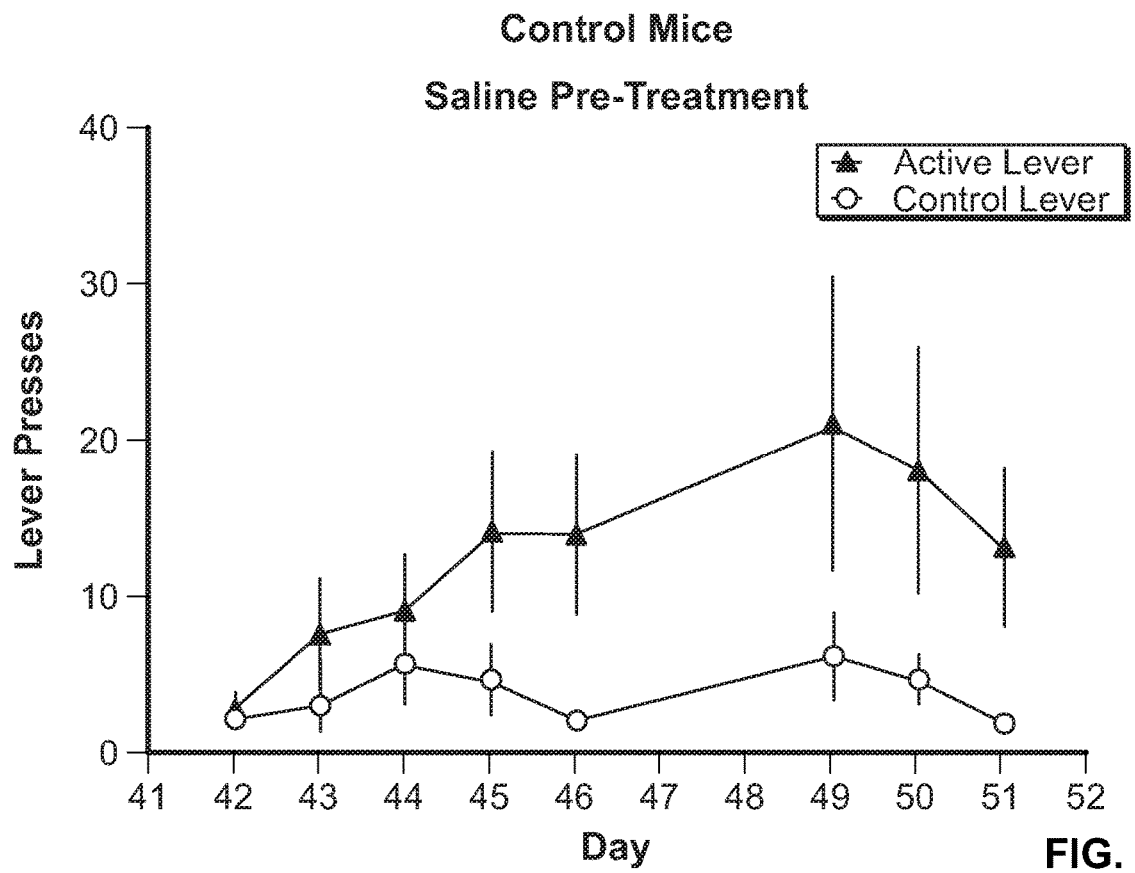
FIGS. 6A and 6B show an in vivo model of opioid addiction in mice.
Figure 6B:
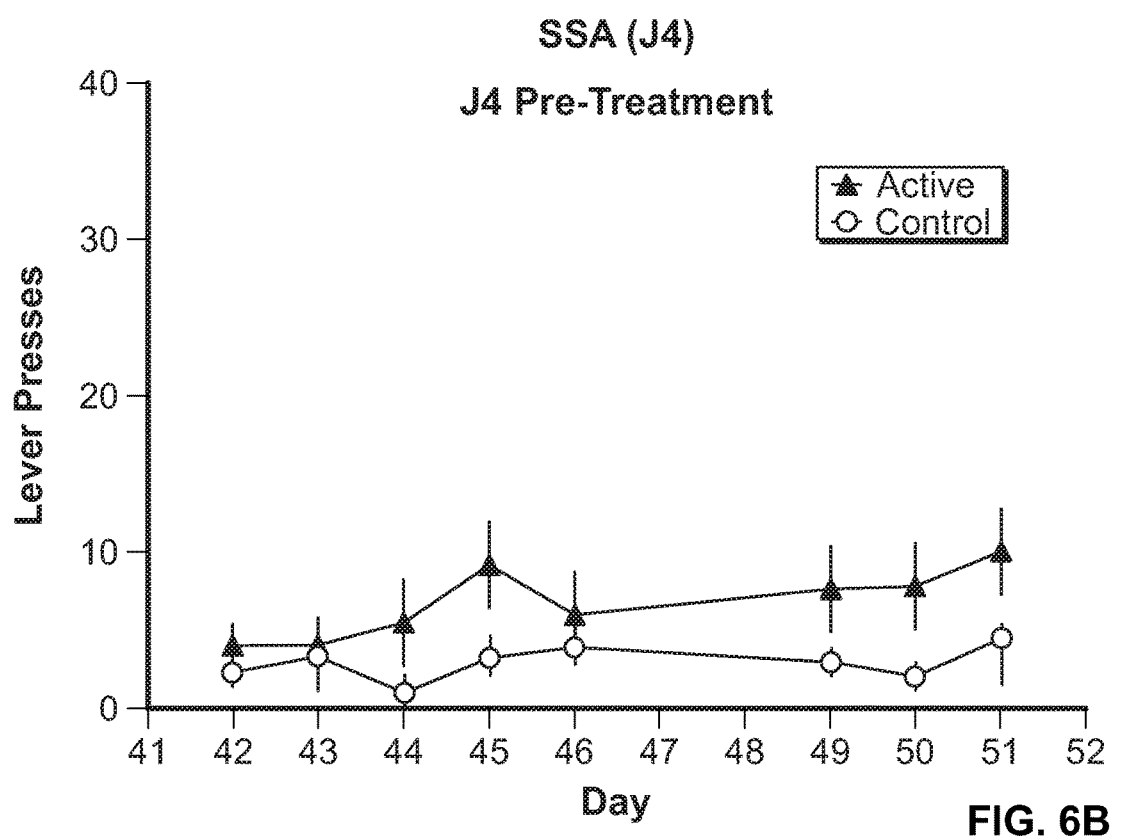

Formula I compounds were assessed for similar effects in a model of oral oxycodone self-administration. In particular, formula I compound J-4 showed activity (FIG. 6) in a pre-clinical model of opioid addiction. Standard enclosed operant conditioning chambers modeled opioid addiction where in response to a light cue, mice have an opportunity to choose between one of two levers. Pressing one lever (the "Active" lever) results in delivery of a small quantity of oxycodone to a drinking receptacle where the mouse can lick or drink the fluid. Pressing the other lever (termed "Control" lever) results in no reward. In this experiment, female mice were separated into two groups; both groups were trained to lever press for oxycodone reward after pressing the "Active" lever of a two lever choice. Initially one lever press results in one delivery of opioid fluid. Pressing the "control" lever offers no reward. The mice learn this quickly and show preference for the "Active" lever over the "control" lever as seen in days 1-15. On day 15, they were required to press the active lever 3 times to seek the reward. Intravenous injections began on day 16 with a 30 mg/kg dose of the J-4 compound. The mice were given six injections over a period of 8 days. A difference was observed in active versus control lever pressing for mice injected intravenously with saline rather than with the test compound. They showed distinct preference for the active lever on most days. In contrast, those mice injected with the test compound, J-4, showed little preference for the lever after injections were initiated. Responses were monitored from Day 20-40 of the experiment. However, with intravenous drug delivery, responses in both groups were blunted due to non-specific effects of the anesthetic (isoflurane) required to perform the IV injection. Additional testing was performed using the intraperitoneal route of administration which does not require anesthesia. These data are featured in FIGS. 6A and 6B. A difference was observed in active versus control lever pressing for mice injected intraperitoneal (IP) with saline rather than with the test compound. They showed distinct preference for the active lever on most days (FIG. 6A). In contrast, those mice were injected with the test compound, J-4, showed greatly reduced preference for the active versus the control lever (FIG. 6B), relative to the saline-pretreatment group of mice). These data provide proof of concept that, like agmatine, the formula I compounds may be effective in reducing opioid addiction.

Systemic or intrathecal therapy with formula I compounds may produce analgesia or antihyperalgesia at both the peripheral nerve terminal and the spinal cord. Routes of administration include both systemic (by mouth or parenteral) and local (intrathecal or epidural) administration. Other methods of treatment may include treatment of opioid analgesic tolerance and addiction. In vivo preclinical experiments may suggest utility in humans. Limited side effects indicate a broad therapeutic window.

Processes for preparing compounds of formula I are provided as further embodiments of the invention and are illustrated by the following procedures in which the meanings of the generic radicals are as given above unless otherwise qualified.

A compound of formula I can be prepared by acylation of agmatine, (1-(4-aminobutyl)guanidine, CAS Registry Number: 306-60-5) or by following the procedures in Example 1.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Administration of Formula I Compounds

Formula I compounds may be locally administered, e.g., intrathecally or epidurally, in combination with a pharmaceutically acceptable formulation for epidural or intrathecal delivery. Local administration of Formula I compounds may be for acute delivery or for chronic delivery.

Formula I compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate: a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392). Geria (U.S. Pat. No. 4,992,478). Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment, mitigation, or prevention of pain. Examples of such agents include analgesic therapeutic agents. Accordingly, in one embodiment the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal.

The ability of a compound of the invention to act as an analgesic may be determined using pharmacological models which are well known to the art, or using the tests and assays described herein.

The invention will now be illustrated by the following non-limiting Examples.

EXAMPLES

Example 1 Synthesis of Formula I Compounds

Synthesis of J-1

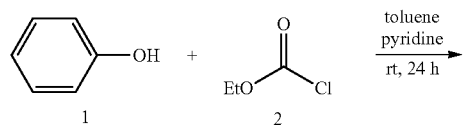

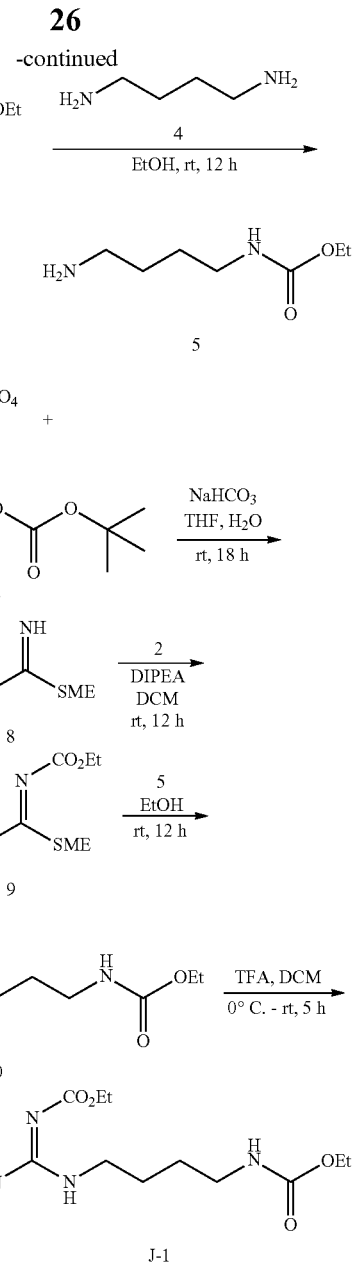

Ethyl Phenyl Carbonate 3 (Shobana, N.; et al, (1988) *Ind. J. Chem. (B Org. Med.)*, 27B:965-966). Phenol 1 (9.4 g, 100 mmol) was reacted with ethyl chloroformate 2 (7.3 g, 67 mmol) in pyridine (5.3 mL) and toluene (100 mL) for 12 h at room temperature. Water (5 mL) was added, and then the organic layer was separated, washed with a HCl solution (5%, 5 mL), a NaOH solution (50%, 5 mL), and water. After drying over $Na_2SO_4$ the solvent was removed under reduced pressure to furnish 3 in near quantitative yield (11 g) as a colorless oil that was used in the next step without further purification. Compound 3 is also commercially available.

Ethyl (3-Aminobutyl)carbamate 5 (Shearman, J. W.; et al (2011) Org. Biomol. Chem., 9:62-65). To a solution of putrescine, butane-1,4-diamine 4 (4.74 g, 53.3 mmol) in absolute ethanol (65 mL) was added dropwise a solution of 3 (8.85 g, 53.3 mmol) in ethanol (10 mL). After stirring at room temperature for 12 h, the solvent was removed under reduced pressure. The residue was taken up into water (100 mL), acidified with HCl (3N) to pH=2-3. The aqueous phase was extracted with CH$_2$Cl$_2$ (3×50 mL) and then a NaOH solution (10%) was added. After extraction with CH$_2$Cl$_2$ (3×50 mL) and drying over Na$_2$SO$_4$ the solvent was removed under reduced pressure to furnish 5 (3.5 g, 41% yield) as a pale, yellow oil that was used without purification in the next step.

N-tert-Butoxycarbonyl-S-methylisothiourea 8 (Kapp, T. G.; et al (2016) *Angew. Chem.*, 128:1564-1568). To a vigorously stirred suspension of S-methylisothiouronium hemisulfate 6 (20.26 g, 146 mmol) in CH$_2$Cl$_2$ (200 mL) in an ice-water bath was added sat. aq. NaHCO$_3$ (150 mL). To the clear solution, di-tert-butyl dicarbonate, Boc$_2$O 7 (31.8 g, 146 mmol) dissolved in CH$_2$Cl$_2$ (75 mL), was added slowly over 1 h. The cooling bath was removed and stirring continued overnight. The layers were separated and the aqueous layer was extracted with CH$_2$Cl$_2$(2×150 mL). The organic layer was washed with water and brine and dried over anhydrous Na$_2$SO$_4$. Hexanes (100 mL) was added and the solution was concentrated under reduced pressure until the product precipitated. The mixture was cooled and 8 was collected by filtration and dried under vacuum (colorless solid). Yield: 11.12 g (40%). Mp 88-90° C. $^1$H NMR (400 MHz, DMSO-d$_6$) δ 8.53 (s, 2H), 2.30 (s, 3H), 1.39 (s, 9H). $^{13}$C NMR (100 MHz, DMSO-d$_6$) δ 171.5, 160.6, 77.7, 27.9, 12.8.

Note: Do not Perform the Reaction Above with Sodium Hydroxide, Because Methylmercaptan Evolves in this Reaction, which is a Highly Dangerous Carcinogenic Gas.

Alternatively, N-mono-t-butoxycarbonyl-S-methylisothiourea 8 and N,N'-bis-t-butoxycarbonyl-S-methylisothiourea 11 can be prepared as follows:

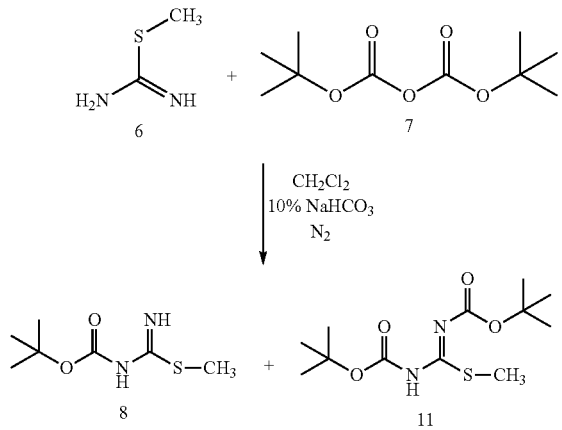

A solution of di-tert-butyl dicarbonate 7 CAS Reg. No. 24424-99-5 (2.44 g, 18.3 mmol) in 50 mL of CH$_2$Cl$_2$ was stirred vigorously under N$_2$. To this was added 5.84 g (26.7 mmol) of S-methylisothiourea 6 but solution did not take place until 50 mL of 10% aq. NaHCO$_3$ solution was added. The mixture was stirred overnight at rt and the layers separated. The aqueous layer was extracted twice with 20 mL of CH$_2$Cl$_2$, and the combined organic phase was washed with about 50 mL of H$_2$O, dried over Na$_2$SO$_4$ and evaporated to dryness on a rotary evaporator to give 4.0 g of colorless solids, which were shown to be two products by thin layer chromatography (tlc). They were separated by column chromatography using silica gel as above to give N,N'-bis-tert-butoxycarbonyl-S-methylisothiourea 11 and N-mono-tert-butoxycarbonyl-S-methylisothiourea 8.

N-tert-Butoxycarbonyl-N'-ethoxycarbonyl-S-methylisothiourea 9 (Pluym, N., et al, (2011) *Chem. Med. Chem.*, 6:1727-1738). To a solution of N-tert-butoxycarbonyl-S-methylisothiourea 8 (1.52 g, 8.0 mmol) in anhydrous CH$_2$Cl$_2$ (30 mL) was added DIPEA (1.05 g, 8.12 mmol) and cooled to 0° C. A solution of 2 (0.868 g, 8.0 mmol) in CH$_2$Cl$_2$ (10 mL) was added slowly, and the reaction mixture was stirred overnight. The reaction mixture was washed with water and brine, then dried over anhydrous Na$_2$SO$_4$. The solvent was removed under reduced pressure and the product was purified by silica gel column chromatography using EtOAc/hexanes (20:80) as the eluent to yield 1.3 g (62%) of 9 as a colorless oil. $^1$H NMR (400 MHz, DMSO-d$_6$) δ 11.01 (s, 1H), 4.06 (q, J=7.0 Hz, 2H), 2.28 (s, 3H), 1.43 (s, 9H), 1.21 (t, J=7.1 Hz, 3H). $^{13}$C NMR (100 MHz, DMSO-d$_6$) δ 165.0, 159.3, 150.1, 82.3, 61.5, 27.5, 14.0, 13.9.

Compound 10. To a solution of 9 (262 mg, 1.0 mmol) in ethanol (10 mL) was added ethyl (3-aminobutyl)carbamate 5 (180 mg, 1.1 mmol) at room temperature. After stirring for 12 h, the solvent was removed under reduced pressure to yield 10 as an oil in quantitative yield and was used without purification in the next step.

Ethyl(amino((4-((ethoxycarbonyl) amino)butyl)amino) methylene)carbamate J-1. Compound 10 (274 mg, 0.732 mmol) was dissolved in CH$_2$Cl$_2$ (10 mL) and then treated with TFA (2 mL). After reaction at room temperature (rt) for 12 h, thin layer chromatography (TLC) indicated complete conversion to J-1. The reaction mixture was poured into a 10% NaHCO$_3$ solution and stirred for 5 min. The organic layer was separated and dried over Na$_2$SO$_4$. Then CH$_2$Cl$_2$ was removed under reduced pressure to furnish J-1 in near quantitative yield as a highly viscous material that solidified in about one week. Mp 89-91.6° C. $^1$H NMR (400 MHz, CDCl$_3$) δ 5.00 (t, J=6.3 Hz, 1H), 4.01 (q, J=7.2 Hz, 4H), 3.17 (p, J=7.0 Hz, 4H), 1.58-1.45 (m, 4H), 1.29-1.08 (m, 6H). $^{13}$C NMR (100 MHz, CDCl$_3$) δ 161.4, 157.4, 61.0, 60.3, 40.5, 39.6, 27.6, 25.8, 14.7, 14.6.

Synthesis of J-2

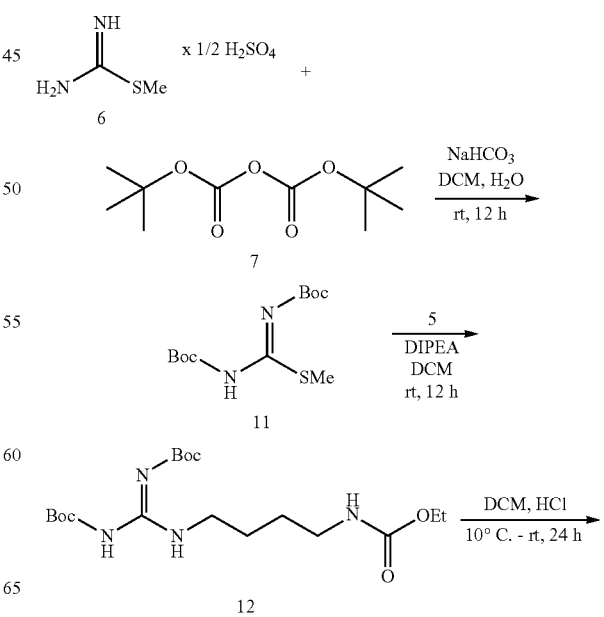

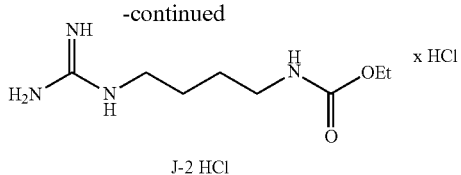

J-2 HCl

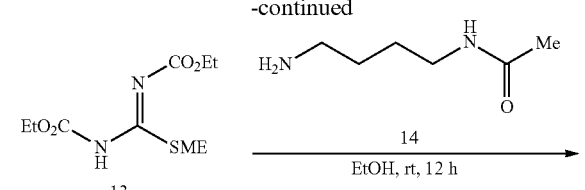

N,N-bis(tert-Butoxycarbonyl)-S-methylisothiourea 11 (Bergeron, R. J.; et al, (1987) *Jour. of Org. Chem.*, 52:1700-1703). S-Methylisothiourea hemisulfate 6 (5.56 g, 40 mmol) was dissolved in a mixture of water (60 mL) and $CH_2Cl_2$ (120 mL) followed by addition of a $NaHCO_3$ solution (3.68 g, 43.8 mmol in 40 mL water) and di-tert-butyl dicarbonate, $Boc_2O$ 7 (23.25 g, 107 mmol). The reaction mixture was vigorously stirred overnight at rt. The layers were separated and the aqueous layer was extracted twice with $CH_2Cl_2$. The combined organic layer was washed with brine, dried over $Na_2SO_4$, filtered and concentrated under reduced pressure. The crude solid was triturated ($EtOH/H_2O$, 1:9, 100 mL) for 1 h and the resulting solid was collected via vacuum filtration and washed with $H_2O$ (4×30 mL) to afford 11 as a fine white powder (5.46 g, 47%). Mp 127° C. Compound 11 is commercially available.

Compound 12. To a solution of N,N-bis(tert-butoxycarbonyl)-S-methylisothiourea 11 (1.0 g, 3.44 mmol) in absolute ethanol (40 mL) was added a solution of ethyl(4-aminobutyl)carbamate 5 (0.606 g, 3.78 mmol) in absolute ethanol (15 mL). The reaction was stirred overnight at rt. The solvent was removed under reduced pressure and the crude product was purified by column chromatography to afford 12 as an oil (0.900 g, 65%) that formed a colorless solid on standing. Mp 88-91° C. $^1$H NMR (400 MHz, DMSO-$d_6$) δ 11.50 (s, 1H), 8.28 (t, J=5.7 Hz, 1H), 7.06 (t, J=5.9 Hz, 1H), 3.97 (q, J=7.1 Hz, 2H), 3.27 (q, J=6.5 Hz, 2H), 2.97 (q, J=6.4 Hz, 2H), 1.48 (s, 11H), 1.40 (s, 11H), 1.15 (t, J=7.0 Hz, 3H). $^{13}$C NMR (100 MHz, DMSO-$d_6$) δ 163.1, 156.2, 155.2, 152.0, 82.8, 78.1, 59.4, 28.2, 28.0, 28.0, 27.6, 26.7, 25.9, 14.6.

Ethyl (4-guanidinobutyl)carbamate J-2 hydrochloride. Product 12 from the previous reaction (0.850 g, 2.11 mmol) was dissolved in dry $CH_2Cl_2$ (40 mL) and cooled to 10° C. before HCl in diethyl ether (2 M, 20 mL) was added slowly. After stirring for 24 h at rt, the solvent was removed under reduced pressure. To the crude mixture was added dry hexanes (30 mL). After stirring for 10 min, the hexanes was decanted. This process was repeated twice. The product was dried under vacuum to give provide J-2 HCl as a viscous oil (0.412 g, 82%). $^1$H NMR (400 MHz, DMSO-$d_6$+$D_2O$) δ 3.93 (q, J=7.0 Hz, 2H), 3.19 (t, J=6.8 Hz 1H), 3.06-3.03 (m, 1H) 2.97-2.94 (m, 2H), 1.42 (s, 4H), 1.10 (t, J=6.9 Hz, 3H). $^{13}$C NMR (100 MHz, DMSO-$d_6$) δ 155.6, 154.97, 82.2, 58.1, 26.3, 25.3, 24.6, 13.4.

Note: In the Reaction Above, Complete Boc Deprotection Using HCl/Diethyl Ether Requires 24 h. At Shorter Reaction Time, Only One Boc Deprotection Takes Place.

Synthesis of J-3

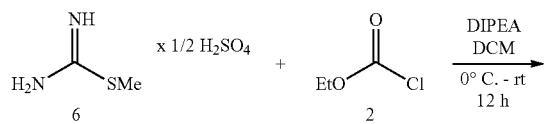

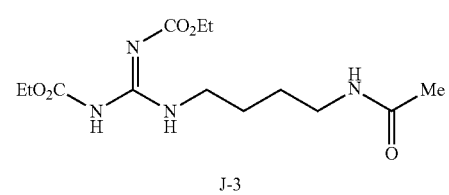

J-3

Compound 13 (US 2006/0025424; Massa, S., et al (1990) *J. Heterocycl. Chem.*, 27:1131-1133). To a suspension of 2-methyl-2-thiopseudourea hemisulfate 6 (7.6 g, 54.6 mmol) in $CH_2Cl_2$ (75 mL) was added DIPEA (15 mL, 10.9 g, 84 mmol) at room temperature then stirred for 10 min. The reaction mixture was cooled to 0° C. and ethyl chloroformate 2 (8.9 g, 82.0 mmol) was added slowly during 10 minutes. After stirring overnight at rt, the mixture was washed with water, and brine, then was dried over sodium sulfate. The solvent was removed under a slight vacuum to yield 13 (10.0 g, 78%) as an oil that solidified on standing, 44.5-46.5° C. $^1$H NMR (400 MHz, DMSO-$d_6$) δ 11.14 (s, 1H), 4.11 (q, J=7.7 Hz, 4H), 2.30 (d, J=1.8 Hz, 3H), 1.22 (t, J=7.2 Hz, 6H). $^{13}$C NMR (100 MHz, DMSO) δ 163.6, 159.1, 151.3, 62.0, 61.5, 14.0, 13.9.

Alternatively, N-mono-ethoxycarbonyl-S-methylisothiourea and N,N'-bis-ethoxycarbonyl-S-methylisothiourea 13 can be prepared from 6 as follows:

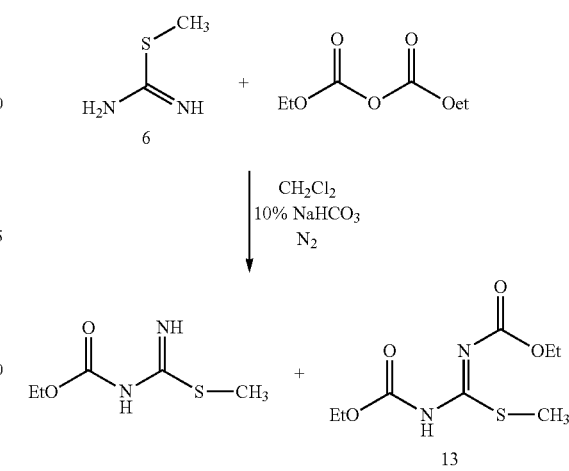

To a solution of diethyl dicarbonate, CAS Reg. No. 1609-47-8 (15.2 g, 93.8 mmol) in 150 mL of $CH_2Cl_2$ (under $N_2$) was added a slurry of 10.9 g (78.3 mmol) of S-methylisothiourea 6, CAS Reg. No. 867-4-7 (hemisulfate salt) in 150 mL of 10% aq. $NaHCO_3$. The isothiourea dispersed and dissolved into the organic phase immediately. The mixture was stirred at room temperature overnight. A TLC (thin layer chromatography) sample of the organic phase showed two distinct product spots, verified to be two products in 1:1 ratio by nmr spectrum.

The products were separated by column chromatography using 325 g of silica gel. The less polar product was eluted with 10% EtOAc-hexane to give 6.30 g of colorless solids (29.1 mmol; 37.6% yield), identified by nmr spectrum to be N,N'-bis-ethoxycarbonyl-S-methylisothiourea 13, mp 42.5-43.5° C. Further elution with 40% EtOAc-hexane provided 4.21 g of colorless solids (26.0 mmol; 37.2% yield), identified by nmr spectrum as, N-mono-ethoxycarbonyl-S-methylisothiourea.

Compound 13 is commercially available.

4-(2,3-Bis(ethoxycarbonyl)guanidino)butylacetamide J-3. To a solution of 13 (2.00 g, 8.54 mmol) in abs, ethanol (15 mL) was added a solution of commercially available N-acetylputrescine 14. CAS Reg. No. 18233-70-0 (1.2 g, 9.2 mmol) in abs, ethanol (10 mL). After the reaction was stirred overnight at rt, the solvent was removed under reduced pressure. Addition of chloroform and evaporation was repeated twice to yield 3.4 g of a viscous oil, which on triturating with hexanes:Et$_2$O (9:1) produced white solids that were separated and washed with hexanes:Et$_2$O (9:1) and dried under vacuum to yield 1.8 g (67%) of J-3 as a colorless solid. Mp 95-97° C. $^1$H NMR (400 MHz, CDCl$_3$) δ 11.70 (s, 1H), 8.36 (t, J=5.7 Hz, 1H), 6.05 (s, 1H), 4.22 (q, J=7.1 Hz, 2H), 4.14 (q, =7.1 Hz, 2H), 3.44 (q, J=6.6 Hz, 2H), 3.29 (q, J=6.4 Hz, 2H), 1.98 (s, 3H), 1.63 (p, J=7.0 Hz, 2H), 1.55 (p, J=7.2 Hz, 2H), 1.30 (td, J=7.1, 2.6 Hz, 6H).

Synthesis of J-4 and J-5

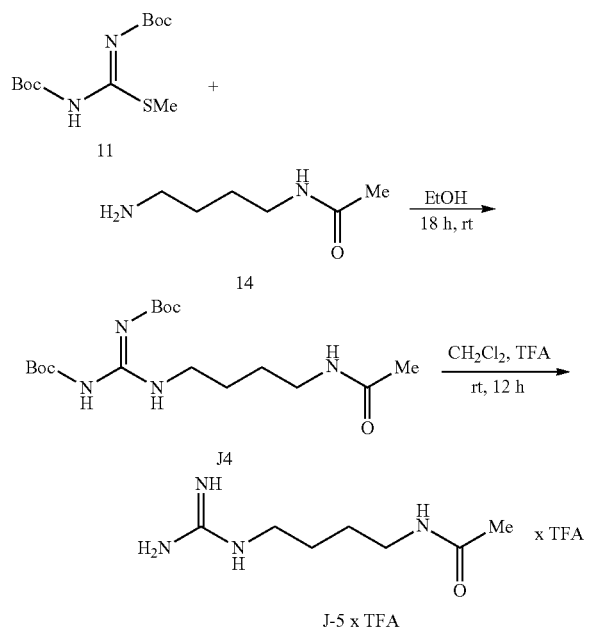

4-(2,3-Bis(tert-butyloxycarbonyl)guanidino)butylacetamide J-4: Commercially available N-acetylputrescine 14 (1.30 g, 1.00 mL, 9.99 mmol, 2.00 equiv) and 1,3-bis(tert-butoxycarbonyl)-2-methyl-2-thiopseudourea 11 (1.45 g, 4.99 mmol, 1.00 equiv) were dissolved in ethanol (95%, 50 mL). The homogeneous solution was stirred overnight (~18 hours) at rt. TLC indicated a complete consumption of starting material (5:4:1 EtOAc/hexanes/MeOH). The reaction mixture was concentrated to furnish a clear oil that was purified by silica gel column chromatography with an isocratic mixture of 5:4:1 EtOAc/hexanes/MeOH to afford 1.01 g (55%) of J-4 as a colorless solid. Mp 122.5-124.5. Anal. Calc'd for C$_{15}$H$_{23}$N$_4$O$_5$: C, 54.82; H, 8.66: N, 15.04. Found: C, 55.08; H, 8.55; N, 15.19. $^1$H NMR (400 MHz, MeOH-d$_4$) δ 3.37 (t, J=6.8 Hz, 2H), 3.20 (t, J=6.6 Hz, 2H), 1.93 (s, 3H), 1.67-1.54 (m, 4H), 1.53 (s, 9H), 1.47 (s, 9H): $^{13}$C NMR (100 MHz, MeOH-d$_4$) δ 173.2, 164.5, 157.6, 154.2, 84.4, 80.3, 41.4, 40.1, 28.6, 28.2, 27.6, 27.5, 22.6.

N-(4-Guanidinobutyl)acetamide Trifluoroacetate, J-5 trifluoroacetate: 4-(2,3-Bis(tert-butyloxycarbonyl)guanidino)butylacetamide J-4 (1.01 g, 2.71 mmol) was dissolved in CH$_2$Cl$_2$ (50 mL) and TFA (10 mL) was added via a steady stream. The reaction mixture was stirred at it overnight. TLC analysis (5:4:1:EtOAc/hexanes/MeOH) showed complete consumption of starting material. The reaction was concentrated to give J-5 trifluoroacetate as a clear viscous oil in quantitative yield. $^1$H NMR (400 MHz, D$_2$O) δ 3.15 (t, J=6.5 Hz, 4H), 1.95 (s, 3H), 1.61-1.45 (m, 4H); $^{13}$C NMR (100 MHz, D$_2$O) δ 174.0, 162.7 (q, J=35.8 Hz), 156.6, 116.2 (q, J=293.4 Hz), 40.7, 38.9, 25.4, 25.2, 21.6.

Synthesis of J-6

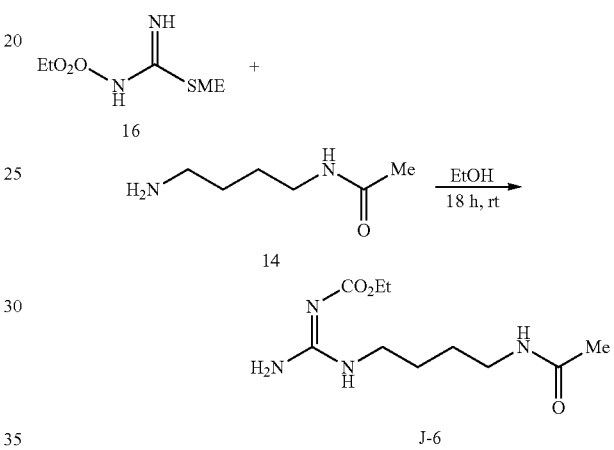

4-(2-(ethoxycarbonyl)guanidino)butylacetamide J-6: Commercially available 16 (0.809 g, 4.99 mmol, 1.00 equiv) and N-acetylputrescine 14 (1.30 g, 1.00 mL, 9.99 mmol, 2.00 equiv) were dissolved in ethanol (95%, 50 mL). The homogeneous solution was stirred overnight (about 18 hours) at rt. TLC indicated a complete consumption of starting material (5:4:1 EtOAc/hexanes/MeOH). The reaction mixture was concentrated to a clear oil which was purified by silica gel column chromatography with an isocratic mixture of 5:4:1 EtOAc/hexanes/MeOH. Concentration of the desired fractions afforded 0.56 g (46%) of J-6 as a cream colored solid. Mp 118-120° C. $^1$H NMR (400 MHz, MeOH-d$_4$) δ 3.97 (q, J=7.1 Hz, 2H), 3.10 (dt, J=9.9, 6.3 Hz, 4H), 1.83 (s, 3H), 1.51-1.41 (m, 4H), 1.15 (t, J=7.1 Hz, 3H). $^{13}$C NMR (100 MHz, MeOH-d$_4$) δ 173.33, 61.66, 41.63, 40.08, 39.93, 28.20, 27.65, 27.54, 22.54, 14.94. MS (LCMS): 245 (M+1)$^+$.

Synthesis of J-7

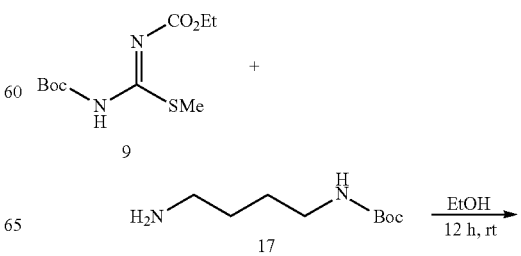

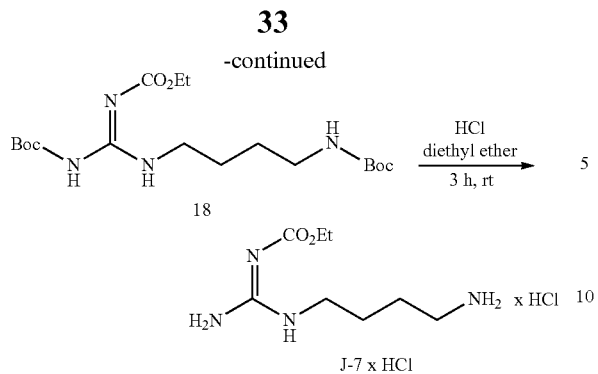

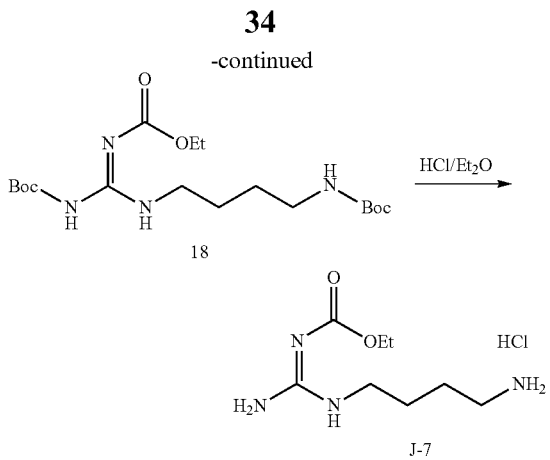

Compound 18. To a solution of N-tert-butoxycarbonyl-N'-ethoxycarbonyl-S-methylisothiourea 9 (1.25 g, 4.76 mmol) in absolute ethanol (40 mL) was added a solution of commercially available tert-butyl (4-aminobutyl)carbamate 17 (0.986 g, 5.23 mmol) in absolute ethanol (15 mL). The reaction was stirred overnight at rt. The solvent was removed under reduced pressure and the crude product was purified by silica gel column chromatography, eluting with EtOAc/hexanes (20:80) to yield 0.756 g (40%) of 18 as an oil. $^1$H NMR (400 MHz. DMSO-$d_6$) δ 11.41 (s, 1H), 8.36 (t, J=5.7 Hz, 1H), 6.78 (t, J=5.8 Hz, 1H), 3.98 (q, J=7.1 Hz, 2H), 3.32-3.24 (m, 3H), 2.90 (q. J=6.5 Hz, 3H), 1.46 (s, 11H), 1.39 (s, 3H), 1.36 (s, 15H), 1.17 (t, J=7.1 Hz, 4H). $^{13}$C NMR (100 MHz, DMSO-d&) δ 163.3, 155.5, 155.3, 151.9, 82.8, 77.3, 60.4, 28.2, 27.5, 26.8, 25.9, 14.3.

4-(2-(Ethoxycarbonyl)guanidino)butan-1-aminium 2,2,2-trifluoroacetate, J-7 hydrochloride. Product 18 from the previous reaction (0.700 g, 1.74 mmol) was dissolved in dry CH$_2$Cl$_2$ (40 mL) and cooled to 10° C. before HCl in Et$_2$O (2 M, 20 mL) was added slowly and stirred for 12 h at rt. After the solvent was removed under reduced pressure, dry ethyl ether (30 mL) was added and the mixture was stirred for 10 min. The solvent was slowly decanted, and this process was repeated twice more to afford a colorless highly hygroscopic solid, which was dried under vacuum to furnish J-7 hydrochloride as a viscous oil (0.360 g, 87%). $^1$H NMR (400 MHz, D$_2$O) δ 4.21 (q, J=7.2 Hz, 2H), 3.32-3.29 (m, 2H), 3.02-2.92 (m, 2H), 1.66 (p, J=3.2 Hz, 4H), 1.22 (t, J=7.2 Hz, 3H). $^{13}$C NMR (100 MHz, DMSO-d$_6$) δ 153.2, 152.5, 62.6, 34.1, 27.6, 24.8, 24.0, 14.0.

Alternatively, J-7 is prepared by the following procedures:

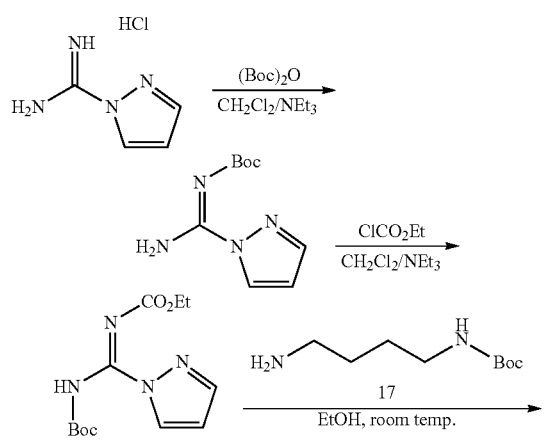

1H-pyrazole-1-carboximidamide hydrochloride is converted to the mono-Boc intermediate, tert-butyl (Z)-(amino (1H-pyrazol-1-yl)methylene)carbamate with di-tert-butyl dicarbonate, Boc$_2$O 7. Acylation with ethylchloroformate 2 gives ethyl-(((tert-butoxycarbonyl)amino)(1H-pyrazol-1-yl)methylene)carbamate. Amination with tert-butyl (4-aminobutyl)carbamate 17 gives 18 which is converted to J-7 as above.

Synthesis of J-8

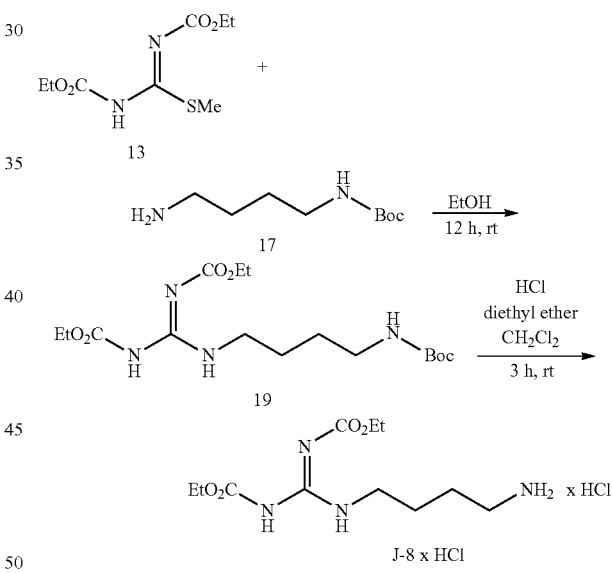

Compound 19. To a solution of 1,3-bis(ethoxycarbonyl)-S-methylisothiourea 13 (1.9 g, 8.11 mmol) in absolute ethanol (20 mL) was added a solution of tert-butyl (4-aminobutyl)carbamate 17 (1.82 g, 9.66 mmol) in absolute ethanol (15 mL). The reaction stirred overnight at rt and then the solvent was removed under reduced pressure. The crude product was purified by silica gel column chromatography using EtOAc/hexanes (20:80) as the eluent to obtain 19 as an oil (650 mg, 21% yield). $^1$H NMR (400 MHz, DMSO-$d_6$) δ 11.57 (s, 1H), 8.35 (t, J=5.7 Hz, 1H), 6.78 (t, J=5.8 Hz, 1H), 4.18 (q, J=7.1 Hz, 2H), 3.99 (q, J=7.1 Hz, 2H), 3.31-3.27 (m, 2H), 2.93-2.88 (m, 2H), 1.51-1.43 (m, 2H), 1.36 (s, 11H), 1.24 (t, J=7.1 Hz, 3H), 1.17 (t, J=7.1 Hz, 3H). $^{13}$C NMR (100 MHz, DMSO-d$_6$) δ 163.3, 155.5, 155.0, 152.8, 77.3, 62.3, 60.4, 59.7, 28.2, 26.7, 25.9, 20.7, 14.3, 13.9.

4-(2,3-Bis(ethoxycarbonyl)guanidino)butan-1-aminium chloride, J-8 Hydrochloride. Product 19 (650 mg, 1.74 mmol) was dissolved in dry CH$_2$Cl$_2$ (50 mL), cooled to 10° C. before slowly adding a HCl solution in Et$_2$O (2 M, 20 mL) and then stirred for 3 h at room temperature. The solvent was removed under reduced pressure and dry ethyl ether (30 mL) was added. The precipitate was collected by filtration and was found to be highly hygroscopic, turning immediately into a light-yellow viscous oil, which was dried under anhydrous conditions and under vacuum to afford J-8×HCl (400 mg, 74% yield) as a yellow highly hygroscopic solid. $^1$H NMR (400 MHz, DMSO-d$_6$) δ 11.59 (s, 1H), 8.74 (s, 1H), 7.94 (s, 3H), 4.20 (q, J=7.1 Hz, 2H), 4.04 (q, J=7.0 Hz, 2H), 3.42-3.29 (m, 2H), 2.78 (bs, 2H), 1.55 (q, J=3.9 Hz, 4H), 1.24 (t, J=7.1 Hz, 3H), 1.19 (t, J=7.1 Hz, 3H).

Synthesis of J-9

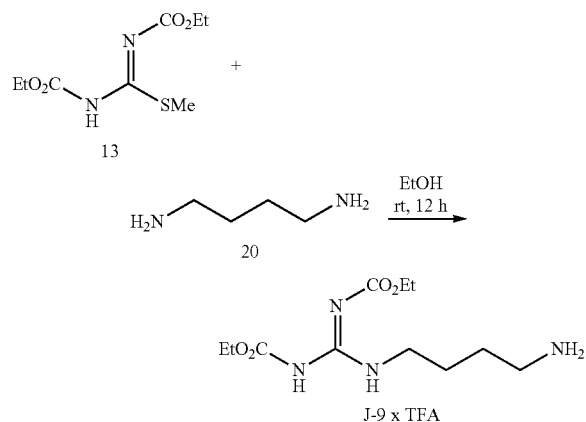

4-(2,3-Bis(ethoxycarbonyl)guanidino)butan-1-aminium 2,2,2-trifluoroacetate, J-9 trifluoroacetate: 1,3-Dicarboethoxy-2-methyl-2-thiopseudourea 13 (2.64 g, 11.3 mmol, 1.00 equiv) and putrescine 20 (20, 2.98 g, 3.40 mL, 33.8 mmol, 3.00 equiv) were dissolved in EtOH (50 mL, 95%). The reaction mixture was allowed to stir overnight at rt. The EtOH was removed under reduced pressure. The crude oil was dissolved in CH$_2$Cl$_2$ (200 mL) and washed trice with H$_2$O. The organic layer was dried, filtered and concentrated to give a clear oil. The clear oil was taken up in CH$_2$Cl$_2$ (20 mL) and TFA (1.73 mL, 2.00 equiv) was added. The reaction was allowed to stir for 3 h and concentrated to give J-9 trifluoroacetate as a clear oil which solidified to a waxy solid upon standing. $^1$H NMR (400 MHz, D$_2$O) δ 4.18 (q, J=7.2 Hz, 4H), 3.99 (m, 2H), 3.04 (m, 2H), 2.92 (m, 2H), 1.74-1.33 (m, 4H), 1.12 (t, J=7.1 Hz, 6H).

Synthesis of J-13

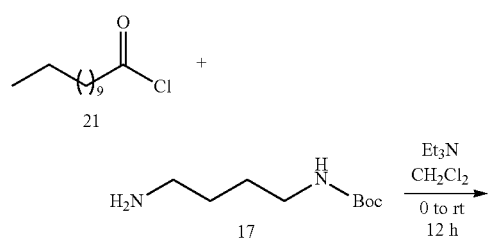

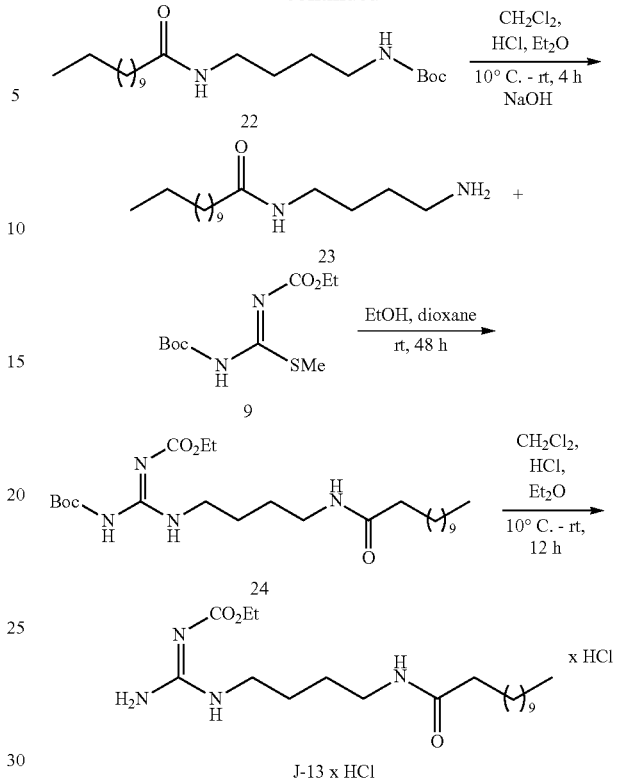

tert-Butyl (4-Dodecanamidobutyl)carbamate 22. To a solution of N-Boc-putrescine 17 (3.0 g, 15.94 mmol) in dry CH$_2$Cl$_2$ (40 mL) and triethylamine (1.7 g, 16.80 mmol) was added a solution of dodecanoyl chloride 21 (3.48 g, 15.90 mmol) in dry CH$_2$Cl$_2$ (30 mL). The reaction was stirred overnight at rt and then the solvent was removed under reduced pressure. The crude product was crystallized from EtOAc/hexanes to afford 22 as a colorless solid (5.31 g, 90%). Mp 94-96. ° C. $^1$H NMR (400 MHz, DMSO-d$_6$) δ 7.71 (t, J=5.7 Hz, 1H), 6.77 (t, J=5.8 Hz, 1H), 3.00 (q, J=5.7 Hz, 2H), 2.89 (q, J=5.9 Hz, 2H), 2.02 (t, J=7.4 Hz, 2H), 1.47 (t, J=7.0 Hz, 2H), 1.37 (s, 9H), 1.34 (t, J=3.0 Hz, 4H), 1.24 (s, 16H), 0.90-0.83 (m, 3H). $^{13}$C NMR (100 MHz, DMSO-d$_6$) δ 171.8, 155.5, 77.3, 38.1, 35.4, 31.3, 30.0, 29.0, 28.9, 28.7, 28.7, 28.6, 28.2, 27.0, 26.6, 25.3, 22.1, 13.9.

N-(4-Aminobutyl)dodecanamide 23 (Ferreira, B, d. S. et al (2014) Boorg. Med. Chem. Lett., 24:4626-4629), tert-Butyl (4-dodecanamidobutyl)carbamate (22, 4.0 g, 10.8 mmol) was dissolved in dry CH$_2$Cl$_2$(50 mL) and cooled to 10° C. before HCl in Et$_2$O (2M, 20 mL) was added slowly and stirred for 4 h at rt. The solvent was removed under reduced pressure, water (50 mL) was added and the solution was cooled to 5° C. and adjusted to pH 10 with a sodium hydroxide solution. The precipitated colorless compound 23 was filtered and dried under vacuum to give 2.48 g (86%) of the targeted product, which was used in the next step without further purification. Mp 136-138° C.

Compound 24. To a solution of 9 (2.41 g, 9.19 mmol) in absolute ethanol (40 mL) was added a solution of N-(4-aminobutyl)dodecanamide 23 (2.48 g, 9.17 mmol) in absolute ethanol (15 mL) and 1,4-dioxane (20 mL). After the reaction was stirred for 48 h at rt, the solvent was removed under reduced pressure. The crude product 24 was purified by silica gel column chromatography, eluting with EtOAc/ hexanes (30:70), to afford a colorless solid (1.5 g, 35%). Mp 38-39° C. ¹H NMR (400 MHz, DMSO-$d_6$) δ 11.42 (s, 1H), 8.37 (t, J=5.7 Hz, 1H), 7.74 (t, J=5.7 Hz, 1H), 4.00 (q, J=7.1 Hz, 2H), 3.30-3.27 (m, 2H), 3.04 (q, J=6.5 Hz, 2H), 2.03 (t, J=7.3 Hz, 2H), 1.48 (s, 11H), 1.40-1.35 (m, 2H), 1.23 (s, 16H), 1.18 (t, J=7.1 Hz, 3H), 0.91-0.82 (m, 3H). ¹³C NMR (100 MHz, DMSO-$d_6$) δ 171.9, 163.3, 155.3, 151.9, 82.9, 60.4, 38.0, 35.4, 31.3, 28.98, 28.95, 28.91, 28.7, 28.7, 28.6, 27.9, 27.6, 26.5, 26.1, 25.3, 22.1, 14.3, 13.9.

6-Imino-4,13-dioxo-3-oxa-5,7,12-triazatetracosane, J-13 hydrochloride. Reaction product 24 (1.3 g, 2.68 mmol) was dissolved in dry $CH_2Cl_2$ (50 mL) and cooled to 10° C. before adding HCl in $Et_2O$ (2 M, 20 mL) slowly. This solution was stirred for 24 h at rt. The solvent was removed under reduced pressure. After dry hexanes (30 mL) was added, stirring continued for 10 min. The colorless solid was filtered and dried under reduced pressure to furnish free amine J-13 as a colorless solid. Mp 118-120° C. ¹H NMR (400 MHz, DMSO-$d_6$) δ 7.75 (t, J=5.8 Hz, 1H), 3.90 (q, J=7.1 Hz, 2H), 3.16-2.97 (m, 4H), 2.03 (t, J=7.4 Hz, 2H), 1.51-1.34 (m, 7H), 1.24 (s, 18H), 1.13 (t, J=7.1 Hz, 3H), 0.86 (t, J=6.5 Hz, 3H). ¹³C NMR (100 MHz, DMSO-$d_6$) δ 172.1, 153.2, 152.5, 62.6, 40.8, 37.7, 35.4, 31.3, 29.0, 29.0, 28.9, 28.8, 28.69, 28.65, 26.2, 25.29, 25.26, 22.1, 14.0, 13.9.

The free amine from the reaction above was dissolved in dry $CH_2Cl_2$ (50 mL) and cooled to 10° C. before adding hydrogen chloride solution in $Et_2O$ (2M, 30 mL) slowly. This solution was stirred for 1 h at rt. The solvent was removed under reduced pressure. After dry hexanes (30 mL) was added, stirring continued for 10 min. The colorless solid was filtered and dried in vacuo afforded J-13 HCl salt as colorless solid (0.990 g, 88% over two steps). Mp 102-104° C. ¹H NMR (400 MHz, DMSO-$d_6$) δ 11.47 (s, 1H), 7.91 (t, J=5.7 Hz, 1H), 4.22 (q, J=7.1 Hz, 2H), 3.30 (q, J=6.6 Hz, 2H), 3.04 (q, J=6.1 Hz, 2H), 2.05 (t, J=7.4 Hz, 2H), 1.54-1.39 (m, 7H), 1.24 (s, 18H), 0.86 (t, J=6.5 Hz, 3H). ¹³C NMR (100 MHz, DMSO-$d_6$) δ 172.1, 153.2, 152.5, 62.6, 40.8, 37.7, 35.4, 31.3, 29.0, 29.0, 28.9, 28.8, 28.69, 28.65, 27.5, 26.2, 25.3, 22.1, 14.0, 13.9.

Example 2. Pharmaceutical dosage forms, containing a compound of Formula I ('Compound X'), for therapeutic or prophylactic use in humans.

| (i) Tablet 1 | mg/tablet |
|---|---|
| formula I compound | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| formula I compound | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| formula I compound | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| formula I compound (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| formula I compound (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| formula I compound | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound selected from:
   ethyl (amino((4-((ethoxycarbonyl)amino)butyl)amino) methylene)carbamate;
   ethyl (4-guanidinobutyl)carbamate;
   4-(2,3-bis(ethoxycarbonyl)guanidino)butylacetamide;
   4-(2,3-bis(tert-butyloxycarbonyl)guanidino)butylacetamide;
   4-(2-(ethoxycarbonyl)guanidino)butylacetamide;
   4-(2-(ethoxycarbonyl)guanidino)butan-1-aminium 2,2,2-trifluoroacetate;
   4-(2,3-bis(ethoxycarbonyl)guanidino)butan-1-aminium chloride;
   4-(2,3-bis(ethoxycarbonyl)guanidino)butan-1-aminium 2,2,2-trifluoroacetate;
   16-carboxy-6-((ethoxycarbonyl)amino)-4, 13-dioxo-3-oxa-5,7,12-triazahexadec-5-en-16-aminium 2,2,2-trifluoroacetate;

(16S,21R)-21-amino-16-((carboxymethyl)carbamoyl)-6-imino-4,13,18-trioxo-3-oxa-14-thia-5,7,12,17-tetraazadocosan-22-oic acid;

21-amino-16-carboxy-6-((ethoxycarbonyl)amino)-4,13,18-trioxo-3-oxa-5,7,12,17-tetraazadocos-5-en-22-oic acid; and 6-imino-4, 13-dioxo-3-oxa-5,7,12-triazatetracosane, or a pharmaceutically acceptable salt thereof.

2. A pharmaceutical composition comprising a compound as described in claim 1 and a pharmaceutically acceptable excipient.

3. A method for treating pain in an animal comprising administering the pharmaceutical composition of claim 2 to the animal.

4. A method for treating or preventing opioid analgesic tolerance, neuropathic pain, and opioid analgesic addiction in an animal comprising administering a compound as described in claim 1, or a pharmaceutically acceptable salt thereof to the animal.

5. The method of claim 4 wherein the compound is administered intrathecally.

* * * * *